United States Patent [19]

Lambert et al.

[11] Patent Number: 4,851,519

[45] Date of Patent: Jul. 25, 1989

[54] PYRIMIDINE DERIVATIVES

[75] Inventors: Robert W. Lambert, Welwyn; Joseph A. Martin, Harpenden; Gareth J. Thomas, Welwyn, all of England

[73] Assignee: Hoffmann-La Roche Inc., Nutley, N.J.

[21] Appl. No.: 80,021

[22] Filed: Jul. 31, 1987

[30] Foreign Application Priority Data

Aug. 18, 1986 [GB] United Kingdom ............... 8620070
May 14, 1987 [GB] United Kingdom ............... 8711336

[51] Int. Cl.$^4$ ................... C07D 405/64; C07H 19/06; A61K 31/70
[52] U.S. Cl. .................................................. 536/23
[58] Field of Search .................. 536/23; 514/49, 50

[56] References Cited

U.S. PATENT DOCUMENTS 4,128,639 12/1978 Lin et al. ........................ 514/50
4,211,773 7/1980 Lopez et al. ..................... 514/49

FOREIGN PATENT DOCUMENTS 3045342 of 0000 Fed. Rep. of Germany .
3045375 7/1982 Fed. Rep. of Germany ........ 514/50

OTHER PUBLICATIONS

Markkham et al., Antiviral Research, 2 319-330 (1982).
Hampton et al., J. Med. Chem., 22, No. 12, 1524-1528 (1979).
CA 98:1372095 (Antiviral Res. 1982, 319-330).
J. Med. Chem. 1986, 1052-1056 (C.A. 104:207594h).
CA 100:156925z (J. Med. Chem. 1984, 27(5), 680-4.
C.A. 82:17034e (J. Che. Soc., Perkin Trans, 1, 1974 (14), 1684-86.
C.A. 106:156807m (J. Med. Chem. 1987, 30(5), 927-30.
C.A. 84:99155y (Ann. N.Y. Acad. Sci. 1975, (255), 33241).
C.A. 90:121985s (U.S. Pat. No. 4,128,639).

Primary Examiner—Herbert J. Lilling
Attorney, Agent, or Firm—Jon S. Saxe; Bernard S. Leon; William G. Isgro

[57] ABSTRACT

Compounds of the formula

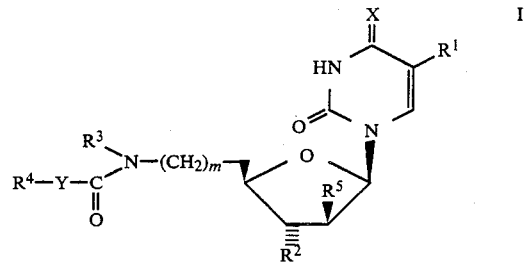

wherein
$R^1$ is halogen, $C_{1-4}$-alkyl, halo-($C_{1-4}$-alkyl) or $C_{2-4}$-alkanoyl,
$R^2$ is hydrogen, hydroxy, $C_{1-4}$alkoxy, $C_{1-4}$-alkylthio or phenyl-($C_{1-4}$-alkoxy) or , when X is O, also acyloxy,
$R^3$ is hydrogen or $C_{1-4}$-alkyl,
$R^4$ is a carbocyclic group or a heterocyclic group,
$R^5$ is hydrogen or fluorine,
m stands for zero, 1 or 2,
X is O or NH and Y is a direct bond, —CH=CH—, —C≡C— or a group of the formula of $$-(Z)_n-A-  \quad\quad (a)$$

in which A is a $C_{1-8}$alkylene group which is optionally substituted by one or two phenyl groups,
Z is O, S, SO or $SO_2$ and n stands for zero or 1, with the proviso that $R^1$ is different from iodine, when $R^2$ is hydroxy or benzoyloxy, $R^3$ is hydrogen,
$R^4$ is unsubstituted phenyl, $R^5$ is hydrogen, m stands for zero, X is O, and Y is a direct bond, and tautomers thereof, which possess antiviral activity and can therefore be used in the form of medicaments for the control and prevention of viral infections are described. The compounds of formula I can be prepared according to known methods.

25 Claims, No Drawings

PYRIMIDINE DERIVATIVES

BRIEF DESCRIPTION OF THE INVENTION

The invention relates to pyrimidine derivatives, a process for their preparation and medicaments containing said derivatives.

The pyrimidine derivatives provided by the invention are compounds of the formula

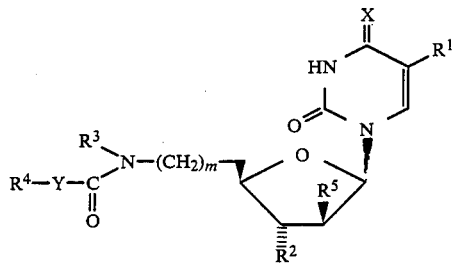

wherein
$R^1$ is halogen, $C_{1-4}$-alkyl, halo-($C_{1-4}$-alkyl) or $C_{2-4}$-alkanoyl,
$R^2$ is hydrogen, hydroxy, $C_{1-4}$-alkoxy, $C_{1-4}$-alkylthio or phenyl-($C_{1-4}$-alkoxy) or, when X is O, also acyloxy,
$R^3$ is hydrogen or $C_{1-4}$-alkyl,
$R^4$ is a carbocyclic group or a heterocyclic group,
$R^5$ is hydrogen or fluorine,
m stands for zero, 1 or 2,
X is O or NH and Y is a direct bond, —CH=CH—, —C≡C— or a group of the formula of $$-(Z)_n-A- \qquad (a)$$

in which A is a $C_{1-8}$-alkylene group which is optionally substituted by one or two phenyl groups.

Z is O, S, So or $SO_2$ and n stands for zero or 1, with the proviso that $R^1$ is different from iodine, when $R^2$ is hydroxy or benzoyloxy, $R^3$ is hydrogen, $R^4$ is unsubstituted phenyl, $R^5$ is hydrogen, m stands for zero, X is O, and Y is a direct bond, and tautomers thereof.

The compounds of formula I and their tautomers possess antiviral activity and can be used in the control, treatment or prevention of viral infection, for example, herpes simplex viral infections.

DETAILED DESCRIPTION OF THE INVENTION

The pyrimidine derivatives provided by the present invention are compounds of the formula

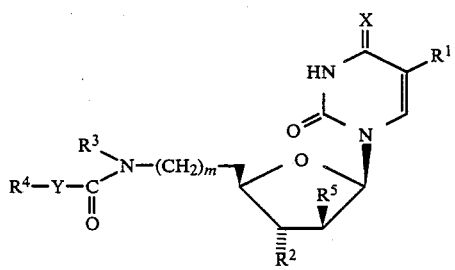

wherein
$R^1$ is halogen, $C_{1-4}$-alkyl, halo-($C_{1-4}$-alkyl) or $C_{2-4}$-alkanoyl,
$R^2$ is hydrogen, hydroxy, $C_{1-4}$-alkoxy, $C_{1-4}$-alkylthio or phenyl-($C_{1-4}$-alkoxy) or, when X is O, also acyloxy,
$R^3$ is hydrogen or $C_{1-4}$-alkyl,
$R^4$ is a carbocyclic group or a heterocyclic group,
$R^5$ is hydrogen or fluorine,
m stands for zero, 1 or 2,
X is O or NH and Y is a direct bond, —CH=CH—, —C≡C— or a group of the formula of $$-(Z)_n-A- \qquad (a)$$

in which A is a $C_{1-8}$-alkylene group which is optionally substituted by one or two phenyl groups, Z is O, S, $SO$ or $SO_2$ and n stands for zero or 1, with the proviso that $R^1$ is different from iodine, when $R^2$ is hydroxy or benzoyloxy, $R^3$ is hydrogen, $R^4$ is unsubstituted phenyl, $R^5$ is hydrogen, m stands for zero, X is O, and Y is a direct bond, and tautomers thereof.

As used therein, the term "$C_{1-4}$-alkyl" taken alone or in combination denotes a straight- or branched-chain alkyl group, such as methyl, ethyl, propyl, isopropyl or t-butyl. Examples of "halo-($C_{1-4}$-alkyl)" groups are trifluoromethyl and 2-chloroethyl. Examples of "$C_{1-4}$-alkylthio" groups are methylthio and ethylthio. Examples of "$C_{1-4}$-alkoxy" groups are methoxy and ethoxy. Examples of "$C_{2-4}$-alkanoyl" groups are acetyl, propionyl and butyryl. Benzyloxy can be mentioned as an example of a phenyl-($C_{1-4}$-alkoxy) group. The acyloxy group can be derived from an aliphatic, cycloaliphatic, araliphatic or aromatic carboxylic acid, examples of such acids are formic acid, acetic acid, propionic acid, butyric acid, t-butylacetic acid, palmitic acid, cyclopentylpropionic acid, phenylacetic acid, benzoic acid and 9-fluorenecarboxylic acid.

The term "carbocyclic group" includes monocyclic and polycyclic aromatic hydrocarbon groups which preferably contain a maximum of 14 carbon atom in the cyclic structure and which can carry one or more substituents selected from the group consisting of halogen, hydroxy, $C_{1-4}$-alkyl, $C_{1-4}$-alkoxy, trifluoro-methyl, phenyl, $C_{1-4}$-alkylphenyl, halophenyl, nitro, amino, acylamino, benzyloxy and O-phosphate for example, phenyl, 2-fluorophenyl, 2-bromophenyl, 2-chlorophenyl, 4-bromophenyl, 2,6-dichlorophenyl, 2,4-dichlorophenyl, 3,5-dichlorophenyl, 4-tolyl, 2,3-dimethylphenyl, 2,6-dimethyl-phenyl, 2,3,5,6-tetramethylphenyl, 2-methoxyphenyl, 3,5-dimethoxyphenyl, 2-trifluoromethylphenyl, 3-trifluoromethylphenyl, 4-trifluoromethylphenyl, 2-nitrophenyl, 3-nitrophenyl, 4-nitrophenyl, 2-aminophenyl, 2-acetamidophenyl, 2-biphenylyl, 4-biphenylyl, 4-chloro-3-nitrophenyl, 2-chloro-4-nitrophenyl, 4-hydroxy-2,6-dimethylphenyl, 3-chloro-4-biphenylyl, 1-naphthyl and 2-naphthyl, and monocyclic and polycyclic cycloalkyl groups which preferably contain a maximum of 13 carbon atoms in the cyclic structure and which, when monocyclic, can carry one or two fused benzene rings, for example, cyclopentyl, cyclohexyl, adamantyl, indanyl and fluorenyl.

The term "heterocyclic group" includes 5- and 6-membered saturated, partially unsaturated and aromatic heterocyclic groups which contain oxygen, nitrogen or sulfur, which can carry a fused benzene ring and which can be substituted by one or more of the substituents mentioned earlier in connection with the carbocyclic group $R^4$. Examples of such heterocyclic groups are 2-furyl, 2-thienyl, 3-thienyl, 2-pyridyl, 3-pyridyl, 2-benzofuranyl, 2,3-dihydro-2-benzofuranyl, 2-benzothienyl, 2-quinolyl and 2-benzopyranyl.

Examples of "$C_{1-8}$-alkylene" groups are —$CH_2$—, —$CH_2CH_2$—, —$CH(CH_3)$—, —$C(CH_3)_2$—, —$CH(C_2H_5)$—, —$CH_2CH_2CH_2$—, —$CH_2$—$CH(CH_3)$— and —$CH_2CH_2CH_2CH_2$—.

It will be appreciated that, depending on the significance of A in formula I, the compounds of this invention can be present as diastereoisomers and that such diastereoisomers also form part of the invention.

In formula I above $R^1$ preferably is $C_{1-4}$-alkyl, especially ethyl or propyl. $R^2$ preferably is hydroxy. $R^3$ preferably is hydrogen. $R^4$ preferably is phenyl optionally substituted by one or more substituents selected from halogen, $C_{1-4}$-alkyl, $C_{1-4}$-alkoxy, trifluoromethyl, phenyl and nitro. Preferably, m stands for zero. X preferably is O. Y preferably is a group of formula (a) above.

Particularly preferred compounds of formula I of the invention are those in which $R^1$ is ethyl, $R^2$ is hydroxy, $R^3$ is hydrogen, $R^4$ is 2-bromophenyl, 2,6-dichlorophenyl or 4-biphenylyl, m stands for zero, X is O and Y is a group of formula (a) in which A is —$CH_2$— or —$CH(CH_3)$— and n stands for zero. Further preferred compounds of formula I of the invention are those in which $R^1$ is ethyl or propyl, $R^2$ is hydroxy, $R^3$ is hydrogen, $R^4$ is 2-biphenylyl, 2,4-dichlorophenyl, 2,4,5-trichlorophenyl, 4-chloro-2-nitrophenyl or 2,4-dichloro-5-methoxyphenyl, m is zero, X is O and Y is a group of formula (a) in which A is —$CH(CH_3)$— or —$CH(phenyl)$—, Z is O and n is 1.

Particularly preferred compounds provided by the invention are:
5'-[2-(2-Bromophenyl)acetamido]-2',5'-dideoxy-5-ethyluridine and
5'-[2-(2,6-dichlorophenyl)acetamido]-2',5'-dideoxy-5-ethyluridine,
5'-[2(RS)-(2,4-dichlorophenoxy)propionamido]-2',5'-dideoxy-5-ethyluridine,
5'-[2-(4-biphenylyl)acetamido]-2',5'-dideoxy-5-ethyluridine.
2',5'-dideoxy-5-ethyl-5'-[2(RS)-(2-phenylphenoxy)propionamido]uridine,
1-[5-[2(RS)-(2,4-dichlorophenoxy)propionamido]-2,5-dideoxy-2-fluoro-β-D-arabinofuranosyl]-5-ethyluracil,
5'-[2(RS)-(2,4,5-trichlorophenoxy)propionamido]-2',5'-dideoxy-5-ethyluridine,
5'-[2(RS)-(4-chloro-2-nitrophenoxy)propionamido]-2',5'-dideoxy-5-ethyluridine,
5'-[2(RS)-(2,4-dichlorophenoxy)-2-phenylacetamido]-2',5'-deoxy-5-ethyluridine,
5'-[2-(RS)-(2,4-dichloro-5-methoxyphenoxy)propionamido]-2',5'-dideoxy-5-ethyluridine and
5'-[2(RS)-(2,4-dichlorophenoxy)propionamido]-2',5'-dideoxy-5-propyluridine.

Examples of other interesting compounds provided by the invention are:
2',5'-Dideoxy-5-ethyl-5'-(2-phenylacetamido)uridine,
5'-(4-bromobenzamido)-5'-deoxythymidine,
5'-deoxy-5'-(4-nitrobenzamido)thymidine,
5'-benzamido-5'-deoxythymidine,
5'-deoxy-5'-(2-fluorobenzamido)thymidine,
5'-deoxy-5'-(2-nitrobenzamido)thymidine,
5'-[2-(2-bromophenyl)acetamido]-5'-deoxythymidine,
5'-deoxy-5'-[2-(4-nitrophenyl)acetamido]thymidine,
5'-deoxy-5'-(2-phenylacetamido)thymidine,
5'-deoxy-5'-[2-(4-trifluoromethylphenyl)acetamido]thymidine,
5'-benzamido-2',5'-dideoxy-5-ethyluridine,
2',5'-dideoxy-5-ethyl-5'-(2-fluorobenzamido)uridine,
5'-(2-bromobenzamido)-2',5'-dideoxy-5-ethyluridine,
2',5'-dideoxy-5-ethyl-5'-(4-nitrobenzamido)uridine,
2',5'-dideoxy-5-ethyl-5'-(2-trifluoromethylbenzamido)uridine,
2',5'-dideoxy-5-ethyl-5'-[2-(2,6-dimethylphenyl)acetamido]uridine,
5'-[2(RS)-(2-bromophenyl)propionamido]-2',5'-dideoxy-5-ethyluridine,
5'-[2-(2-chloro-3-nitrophenyl)acetamido]-2',5'-dideoxy-5-ethyluridine,
5'-[2(RS)-(2,6-dichlorophenyl)propionamido]-2',5'-dideoxy-5-ethyluridine,
2',5'-dideoxy-5-ethyl-5'-[2-(3,5-dimethylphenyl)acetamido]uridine,
2',5'-dideoxy-5'-[2-(3,5-dimethoxyphenyl)acetamido]-5-ethyluridine,
2',5'-dideoxy-5-ethyl-5'-[2-(2,3,5,6-tetramethylphenyl)acetamido]uridine,
2',5'-dideoxy-5-ethyl-5'-[2-(2-methoxyphenyl)acetamido]uridine,
2',5'-dideoxy-5-ethyl-5'-[2-(2-nitrophenyl)]acetamidouridine,
5-bromo-5'-(2-(2-bromophenyl)acetamido]-2',5'-dideoxyuridine,
3'-O-butyryl-5'-[2-(2,6-dichlorophenyl)acetamido]-2',5'-dideoxy-5-ethyluridine,
2',5'-dideoxy-5'-[2-(2,6-dichlorophenyl)acetamido]-3'-O-(3,3-dimethylbutyryl)-5-ethyluridine,
5'-[2-(2,6-dichlorophenyl)acetamido]-2',5'-dideoxy-5-ethyl-3'-O-palmitoyluridine,
3'-O-acetyl-5'-[2-(2,6-dichlorophenyl)acetamido]-2',5'-dideoxy-5-ethyluridine,
3'-O-benzyl-5'-[2-(2,6-dichlorophenyl)acetamido]-2',5'-dideoxy-5-ethyluridine,
5'-[2-(2,6-dichlorophenyl)acetamido]-2',5'-dideoxy-3'-O-ethyl-5-ethyluridine,
2',3',5'-trideoxy-5'-[2-(2,6-dichlorophenyl)acetamido]-5-ethyluridine,
5'-[2-(2-aminophenyl)acetamido]-2',5'-dideoxy-5-ethyluridine,
5'-[2-(2-acetamidophenyl)acetamido]-3'-O-acetyl-2',5'-dideoxy-5-ethyluridine,
5'-[2-(2-acetamidophenyl)acetamido]-2',5'-dideoxy-5-ethyluridine,
2',5'-dideoxy-5-ethyl-5'-[2-(4-hydroxy-2,6-dimethylphenyl)acetamido]uridine,
5-(2-chloroethyl)-5'-[2-(2,6-dichlorophenyl)acetamido]-2',5'-dideoxyuridine,
5'-[2-(2-bromophenyl)-N-methylacetamido]-2',5'-dideoxy-5-ethyluridine,
5'-[2-(2,6-dichlorophenyl)-N-methylacetamido]-2',5'-dideoxy-5-ethyluridine,
5'-[2(RS)-(2-bromophenyl)-N-methylpropionamido]-2',5'-dideoxy-5-ethyluridine,
3'-O-acetyl-5'-[2-(2-bromophenyl)-N-methylacetamido]-2',5'-dideoxy-5-ethyluridine,
2',5'-dideoxy-5-ethyl-5'-(2-naphthalamido)uridine,
2',5'-dideoxy-5-ethyl-5'-(2-phenylbenzamido)uridine,
2',5'-dideoxy-5-ethyl-5'-(3-phenylpropionamido)uridine,
2',5'-dideoxy-5-ethyl-5'-(4-phenylbutyramido)uridine,
2',5'-dideoxy-5'-cinnamamido-5-ethyluridine,
2',5'-dideoxy-5-ethyl-5'-(3-phenyl-2-propynamido)uridine, 2',5'-dideoxy-5-ethyl-5'-[3-(phenylsulfonyl)propionamido]uridine,
5'-(2-bromocinnamamido)-2',5'-dideoxy-5-ethyluridine,
2',5'-dideoxy-5-ethyl-5'-[2-(2-thienyl)acetamido]uridine,
2',5'-dideoxy-5-ethyl-5'-[2-(3-thienyl)acetamido]uridine,
5'-(1-adamantylcarboxamido)-2',5'-dideoxy-5-ethyluridine,
2',5'-dideoxy-5-ethyl-5'-(2-pyridylcarboxamido)uridine,
2',5'-dideoxy-5-ethyl-5'-(3-pyridylcarboxamido)uridine,
2',5'-dideoxy-5-ethyl-5'-[2-(phenylsulphonyl)acetamido]uridine,
2',5'-dideoxy-5-ethyl-5'-(9-fluorenylcarboxamido)uridine,
3'-O-acetyl-2',5'-dideoxy-5-ethyl-5'-(9-fluorenylcarboxamido)uridine,
3'-O-butyryl-2',5'-dideoxy-5-ethyl-5'-(9-fluorenylcarboxamido)uridine,
2',5'-dideoxy-5-ethyl-3'-O-(3,3-dimethylbutyryl)-5'-(9-fluorenylcarboxamido)uridine,
2',5'-dideoxy-5-ethyl-5'-(9-fluorenylcarboxamido)-3'-O-(hexadecanoyl)uridine,
2',5'-dideoxy-5-ethyl-3'-O-(9-fluorenylcarbonyl)-5'-(9-fluorenylcarboxamido)uridine,
2',5'-dideoxy-5-ethyl-5'-(2-phenylbutyramido)uridine,
2',5'-dideoxy-5-ethyl-5'-(3-phenylbutyramido)uridine,
2',5'-dideoxy-5-ethyl-5'-(2,2-diphenylacetamido)uridine,
5'-(2-cyclohexyl-2-phenylacetamido)-2',5'-dideoxy-5-ethyluridine,
2',5'-dideoxy-5'-ethyl-5'-(triphenylacetamido)uridine,
2',5'-dideoxy-5-ethyl-5'-(2-methyl-2-phenylpropionamido)uridine,
2',5'-dideoxy-5-ethyl-5'-[2(RS)-phenylpropionamido)]uridine,
5'-[2(RS)-(2,4-dichlorophenoxy)propionamido]-2',5'-dideoxy-5-ethyluridine,
5'-[2(RS)-(2,6-dichlorophenoxy)propionamido]-2',5'-dideoxy-5-ethyluridine,
5'-[2(RS)-(3,5-dichlorophenoxy)propionamido]-2',5'-dideoxy-5-ethyluridine,
5'-[2(RS)-(2-chlorophenoxy)propionamido]-2',5'-dideoxy-5-ethyluridine,
5'-[2-(2,6-dichlorophenoxy)acetamido]-2',5'-dideoxy-5-ethyluridine,
5'-[2-(2,4-dichlorophenoxy)acetamido]-2',5'-dideoxy-5-ethyluridine,
5'-[4-(2,6-dichlorophenoxy)butyramido]-2',5'-dideoxy-5-ethyluridine,
5'-[6-(2,6-dichlorophenoxy)hexanamido]-2',5'-dideoxy-5-ethyluridine,
5'-[5-(2,6-dichlorophenoxy)valeramido]-2',5'-dideoxy-5-ethyluridine,
5'-[2(RS)-(2-chloro-4-nitrophenoxy)propionamido]-2',5'-dideoxy-5-ethyluridine,
5'-[2(RS)-(2-chloro-4-phenylphenoxy)propionamido]-2',5'-dideoxy-5-ethyluridine
5-bromo-5'-[2-(2-bromophenyl)acetamido]-2',5'-dideoxycytidine, and
5'-[2-(2-bromophenyl)acetamido]-2',5'-dideoxy-5-ethylcytidine.

Examples of additional, interesting compounds provided by the invention are:
5'-[2-(2,6-dichlorophenyl)acetamido]-5'-deoxythymidine,
5-bromo-5'-[2(RS)-(2,,4-dichlorophenoxy)propionamido]-2',5'-dideoxyuridine,
5-bromo-5'-[2-(2,6-dichlorophenyl)acetamido]-2',5'-dideoxyuridine,
5'-benzamido-5-bromo-2',5'-dideoxyuridine,
5'-[2(RS)-(2,4-dichlorophenoxy)propionamido]-2',5'-dideoxy-5-iodouridine,
5'-[2(RS)-(2,4,5-trichlorophenoxy)propionamido]-2',5'-dideoxy-5-iodouridine,
5'-[2-(2,6-dichlorophenyl)acetamido]-2',5'-dideoxy-5-iodouridine,
3'-O-benzyl-5'-[2(RS)-(2,4-dichlorophenoxy)propionamido]-2',5'-dideoxy-5-ethyluridine,
5'-[2(RS)-(2,4-dichlorophenoxy)propionamido]-2',5'-dideoxy-3'-O-ethyl-5-ethyluridine,
5'-[2(RS)-(2,4-dichlorophenoxy)-N-methylpropionamido]-2',5'-dideoxy-5-ethyluridine,
5'-[2(R)-(2,4-dichlorophenoxy)propionamido]-2',5'-dideoxy-5-ethyluridine,
5'-[2(S)-(2,4-dichlorophenoxy)propionamido]-2',5'-dideoxy-5-ethyluridine,
5'-[2(RS)-(2,4-dichlorophenoxy)butyramido]-2',5'-dideoxy-5-ethyluridine,
5'-[2(RS)-(4-acetamido-2-chlorophenoxy)propionamido]-2',5'-dideoxy-5-ethyluridine.
5'-[2(RS)-(2-chloro-4-methoxyphenoxy)propionamido]-2',5'-dideoxy-5-ethyluridine,
2',5'-dideoxy-5-ethyl-5'-[2(RS)-(2-methylbiphenylyloxy)propionamido]uridine,
5'-[2(RS)-(2,4-dichlorophenoxy)propionamido]-5'-deoxythymidine,
5'-[2-(2,4-dichlorophenoxy)-2-methylpropionamido]-2',5'-dideoxy-5-ethyluridine,
2',5'-dideoxy-5-ethyl-5'-[2(RS)-phenoxypropionamido]uridine,
2',5'-dideoxy-5-ethyl-5'-[2(RS)-(2-fluorophenoxy)propionamido]uridine,
2',5'-dideoxy-5-ethyl-5'-[2(RS)-(2-trifluoromethylphenoxy)propionamido]uridine,
1-[5-[2(RS)-(2,4-dichlorophenoxy)propionamido]-2,5-dideoxy-2-fluoro-β-D-arabinofuranosyl]thymine,
5'-[2(RS)-(2,4-dichlorophenylsulphinyl)propionamido]2',5'-dideoxy-5-ethyluridine,
5'-[2(RS)-(2,4-dichlorophenylsulphonyl)propionamido]-2',5'-dideoxy-5-ethyluridine,
5'-[2-(2,6-dichlorophenylacetamido)ethyl]-2',5'-dideoxy-5-ethyluridine,
5'-[2-[2(RS)-(2,4,5-trichlorophenoxy)propionamido]ethyl]-2',5'-dideoxy-5-ethyluridine,
5'-[2-[2(RS)-(2,4-dichlorophenoxy)propionamido]ethyl]-2',5'-dideoxy-5-ethyluridine,
5'-[2(RS)-(2,6-dichlorobenzyl)propionamido]-2',5'-dideoxy-5-ethyluridine,
5'-[2(RS)-(2,4-dichlorobenzyl)propionamido]-2',5'-dideoxy-5-ethyluridine,
5'-[5-chloro-2,3-dihydro-2-(RS)-benzofuranylcarboxamido]-2',5'-dideoxy-5-ethyluridine,
5-(6-chloro-2H-1-benzopyran-2-ylcarboxamido)-2',5'-dideoxy-5-ethyluridine,
5'-[2-(4-benzyloxy-2,6-dimethylphenyl)acetamido]-2',5'-dideoxy-5-ethyluridine,
3'-O-acetyl-5'-[2-(4-benzyloxy-2,6-dimethylphenyl)acetamido]-2',5'-dideoxy-5-ethyluridine,
3'-O-acetyl-2',5'-dideoxy-5-ethyl-5'-[2-(4-hydroxy-2,6-dimethylphenyl)acetamido]uridine,
2',5'-dideoxy-5-ethyl-5'-[2-(2,6-dimethyl-4-phosphatophenyl)acetamido]uridine,
5-(2-chloroethyl)-2',5'-dideoxy-5'-[2-(2,4-dichlorophenyl)propionamido]uridine,
5'-benzamido-5-(2-chloroethyl)-2',5'-dideoxyuridine, 5-(2-chloroethyl)-5'-[2-(2,4,5-trichlorophenoxy)propionamido]-2',5'-dideoxyuridine,
5'-[2-(2,6-dichlorophenyl)acetamido]-2',5'-dideoxy-5-propyluridine,
5'-[2(RS)-(2,4-dichlorophenoxy)propionamido]-2',5'-dideoxy-5-propyluridine and
5-acetyl-5'-[2-(2,6-dichlorophenyl)acetamido]-2',5'-dideoxyuridine.

According to the process provided by the present invention, the compounds of formula I above and their tautomers can be prepared by (a) reacting a compound of the formula

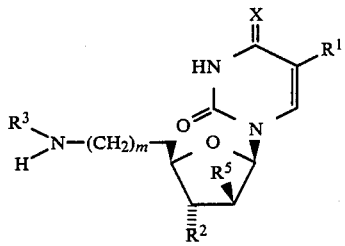

wherein $R^1$, $R^2$, $R^3$, $R^5$, m and X have the significance given earlier, or a tautomer thereof in which any 4-amino group present is optionally protected, with a reactive derivative of an acid of the formula $$R^4-Y-COOH \qquad III$$

wherein $R^4$ and Y have the significance given earlier, and cleaving any protecting group present in the product, or (b) for the preparation of a compound of formula I or a tautomer thereof in which X is O and $R^2$ is acyloxy, acylating a compound of formula I or a tautomer thereof in which X is O and $R^2$ is hydroxy, or (c) for the preparation of a compound of formula I or a tautomer thereof in which X is O and $R^2$ is hydroxy, deacylating a compound of formula I or a tautomer thereof in which X is O and $R^2$ is acyloxy, or (d) for the preparation of a compound of formula I or a tautomer thereof in which Y is a group of formula (a) in which Z is SO or $SO_2$ and n stands for 1, oxidizing a compound of formula I or a tautomer thereof in which Y is a group of formula (a) in which Z is S and n stands for 1, and (e) if desired, functionally modifying a reactive substituent present in $R^4$.

A 4-amino group present in a starting material used in embodiment (a) the above process, that is, in a cytidine derivative, can be protected by a readily cleavable protecting group, particularly an acyl group and especially a benzoyl group.

The reactive derivative of an acid of formula III can be any conventional reactive derivative, for example, an acid halide, an acid anhydride or a reactive derivative formed by activating the acid with dicyclohexylcarbodiimide or a similar activating reagent. In a preferred embodiment, an acid halide, particularly an acid chloride, is used as the reactive derivative.

The reaction in accordance with embodiment (a) of the process can be carried out in a known manner. The reaction can be carried out in the presence or absence of an inert organic solvent. When such a solvent is used, this can suitably be an ether such as diethyl ether, an aromatic hydrocarbon such as benzene, or the like. The reaction is expediently carried out in the presence of an inorganic base such as an alkali metal hydroxide, for example, sodium hydroxide or potassium hydroxide, or a tertiary organic base, for example, pyridine. Conveniently, the reaction is carried out at a temperature in the range of from about 0° C. to room temperature.

When a starting material containing a protected 4-amino group is used, the protecting group is cleaved from the reaction product in a conventional manner. For example, an acyl group such as the benzoyl group can be cleaved by treatment with alcoholic ammonia solution, particularly methanolic ammonia solution, at about room temperature.

The acylation in accordance with embodiment (b) of the process can also be carried out in a known manner, for example, using an appropriate reactive derivative of an acid such as an acid halide, for example, an acid chloride, an acid anhydride or the like. Suitably, the acylation is carried out in the presence of a base, which is suitably a tertiary organic base such as pyridine, 4-dimethylaminopyridine or the like and at a temperature in the range of from about 0° C. to room temperature.

The deacylation in accordance with embodiment (c) of the process can likewise be carried out in a known manner, for example, using an alcoholic ammonia solution, for example, a methanolic ammonia solution, at about room temperature.

The oxidation in accordance with embodiment (d) of the process can also be carried out in a known manner. For example, the oxidation can be carried out using an organic peracid such as peracetic acid, perbenzoic acid, m-chloroperbenzoic acid, perphthalic acid or the like, expediently in a suitable solvent such as a halogenated hydrocarbon, for example, chloroform, or an alkanoic acid, for example, acetic acid, and at a temperature in the range of from about 0° C. to room temperature. When peracetic acid is used for the oxidation, this can conveniently be prepared in situ from glacial acetic acid and hydrogen peroxide. When 1 equivalent of an organic peracid is used there is obtained a compound of formula I or a tautomer thereof in which Z represents —SO—, whereas the use of 2 equivalents of organic peracid leads to a compound of formula I or a tautomer thereof in which Z represents —$SO_2$—.

In accordance with embodiment (e) of the process a reactive substituent present in $R^4$ can be functionally modified. Such modifications can be carried out according to known procedures. For example, when $R^4$ contains a nitro group, this can be reduced by catalytic hydrogenation to an amino group. Again, when $R^4$ contains an amino group, this can be acylated to an acylamino group. Further, when $R^4$ contains a benzyloxy group, this can be converted into a hydroxy group by debenzylation using hydrogen in the presence of a catalyst. Yet again, when $R^4$ contains a hydroxy group, this can be converted into an O-phosphate group by treatment with dibenzylphosphoryl chloride followed by debenzylation using hydrogen in the presence of a catalyst.

The starting materials used in the process provided by the invention are known compounds or analogs of known compounds which can be prepared in a similar manner to the known compounds. Further, certain of the Examples hereinafter contain detailed information concerning the preparation of the respective starting materials.

The compounds of formula I and their tautomers possess antiviral activity and can be used in the control or prevention of viral infections, for example, herpes simplex viral infections.

The in vitro activity of the compounds of formula I and their tautomers in inhibiting herpes simplex virus type 2 (HSV-2) thymidine kinase can be demonstrated by means of the following test procedure:

In this test, the assay mixture contains 50 nM Tris-HCl, pH 8, 5 mM magnesium chloride, 5 mM ATP, 0.3 $\mu$M $^3$H-thymidine (50 Ci/mmol), suitably diluted thymidine kinase extract and various concentrations of a compound of formula I or a tautomer thereof in a total volume of 100 $\mu$l. Assays are incubated at 37° C. for 30 minutes and the reaction is terminated by immersion in a boiling water bath for 2 minutes. 85 $\mu$l aliquots from each assay are then dried on to DEAE-cellulose paper discs and the unphosphorylated $^3$H-thymidine is removed by washing in 4 mM ammonium formate. The radioactivity remaining bound to the discs is then measured by scintillation spectrophotometry. The degree of inhibition at each concentration of compound of formula I or tautomer thereof is expressed as a percentage of the control reaction (100%) after substracting a measured blank value which represents the amount of radioactivity bound to the disc from a reaction containing heat inactivated enzymes. the IC$_{50}$ value, namely, the concentration of compound of formula I or tautomer thereof which inhibits enzyme activity by 50%, is then calculated. The results obtained with representative compounds of formula I are complied in the following Table:

Table

| Compound of formula I | IC$_{50}$ ($\mu$M) |
|---|---|
| A | 0.02 |
| B | 0.003 |
| C | 0.0037 |
| D | 0.07 |
| E | 0.005 |
| F | 0.004 |
| G | 0.0013 |
| H | 0.0027 |
| I | 0.0047 |
| J | 0.0012 |
| K | 0.0035 |

Compound A: 5'-[2-(2-Bromophenyl)acetamido]-2',5'-dideoxy-5-ethyluridine.
Compound B: 5'-[2-(2,6-Dichlorophenyl)acetamido]-2',5'-dideoxy-5-ethyluridine.
Compound C: 5'-[2(RS)-(2,4-Dichlorophenoxy)propionamido]-2',5'-dideoxy-5-ethyluridine.
Compound D: 5'-[2-(4-Biphenylyl)acetamido]-2',5'-dideoxy-5-ethyluridine.
Compound E: 2',5'-Dideoxy-5-ethyl-5'-[2(RS)-(2-phenylphenoxy)propionamido]uridine.
Compound F: 1-[5-[2(RS)-(2,4-Dichlorophenoxy)propionamido]-2,5-dideoxy-2-fluoro-$\beta$-D-arabinofuranosyl]-5-ethyluracil.
Compound G: 5'-[2(RS)-(2,4,5-Trichlorophenoxy)propionamido]-2',5'-dideoxy-5-ethyluridine.
Compound H: 5'-[2(RS)-(4-Chloro-2-nitrophenoxy)propionamido]-2',5'-dideoxy-5-ethyluridine.
Compound I: 5'-[2(RS)-(2,4-Dichlorophenoxy)-2-phenylacetamido]-2',5'-deoxy-5-ethyluridine.
Compound J: 5'-[2(RS)-(2,4-Dichloro-5-methoxyphenoxy)propionamido]-2',5'-dideoxy-5-ethyluridine.
Compound K: 5'-[2(RS)-(2,4-Dichlorophenoxy)propionamido]-2',5'-dideoxy-5-propyluridine.

The compounds of formula I and their tautomers can be used as medicaments in the form of pharmaceutical preparations which contain them in association with a compatible pharmaceutical carrier material. This can be an organic or inorganic carrier suitable for enteral, for example, oral or parenteral administration. Examples of such carriers are water, gelatin, gum arabic, lactose, starch, magnesium stearate, talc, vegetable oils, polyalkylene glycols and petroleum jelly. The pharmaceutical preparations can be made up in a solid form, for example, as tablets, dragees, suppositories or capsules, or in a liquid form, for example, as solutions, suspensions or emulsions, they may be subjected to standard pharmaceutical operations, for example, sterilization and/or may contain adjuvants, for example, preserving, stabilizing, wetting or emulsifying agents, salts for varying the osmotic pressure or buffers. They may also contain other therapeutically valuable substances.

The compounds of formula I and their tautomers can be administered to an adult warm-blooded animal in a daily dosage of from about 1 mg to 1000 mg, preferably about 5 mg to 500 mg. The daily dosage may be administered as a single dose or in divided doses. The above dosage range is given by way of example only and can be varied upwards or downwards depending on factors such as the particular compound being administered, the route of administration, the severity of the indication being treated and the condition of the patient.

The examples which follow further illustrate the invention. All temperatures are in degrees centigrade, unless otherwise stated.

EXAMPLE 1

(A) A solution of 219 mg of 4-bromobenzoyl chloride in 5 ml of diethyl ether was added to a solution of 241 mg of 5'-amino-5'-deoxythymidine in 4 ml of 0.25M sodium hydroxide solution and the mixture was shaken vigorously for 10 minutes. The mixture was filtered and the solid was washed with 10 ml of water and 4 ml of diethyl ether, and recrystallized from ethanol to give 195 mg of 5'-(4-bromobenzamido)-5'-deoxythymidine of melting point 250.5°–252° C.

(B) In an analogous manner, there were obtained:
(a) from 4-nitrobenzoyl chloride and 5'-amino-5'-deoxythymidine: 5'-deoxy-5'-(4-nitrobenzamido)-thymidine, mp 230° C.;
(b) from benzoyl chloride and 5'-amino-5'-deoxythymidine: 5'-benzamido-5'-deoxythymidine, mp 234°–235° C.;
(c) from 2-fluorobenzoyl chloride and 5'-amino-5'-deoxythymidine: 5'-deoxy-5'-(2-fluorobenzamido)-thymidine, mp 228°–228.5° C.; and
(d) from 2-nitrobenzoyl chloride and 5'-amino-5'-deoxythymidine: 5'-deoxy-5'-(2-nitrobenzamido)-thymidine, mp 190°–191° C.

EXAMPLE 2

(A) 140 mg of benzoyl chloride were added to a solution of 255 mg of 5'-amino-2',5'-dideoxy-5-ethyluridine in 3 ml of 0.33M sodium hydroxide solution and the mixture was shaken vigorously for 5 minutes. The mixture was filtered and the solid was washed with 5 ml of water and 5 ml of diethyl ether, and recrystallized from ethanol to give 140 mg of 5'-benzamido-2',5'-dideoxy-5-ethyluridine of melting point 246°–247° C.

(B) In an analogous manner, there were obtained:
(a) from 2-fluorobenzoyl chloride and 5'-amino-2',5'-dideoxy-5-ethyluridine: 2',5'-dideoxy-5-ethyl-5'-(2-fluorobenzamido)uridine, mp 216°–216.5° C.;
(b) from 2-bromobenzoyl chloride and 5'-amino-2',5'-dideoxy-5-ethyluridine: 5'-(2-bromobenzamido)-2',5'-dideoxy-5-ethyluridine, mp 237°–238° C.;
(c) from 4-nitrobenzoyl chloride and 5'-amino-2',5'-dideoxy-5-ethyluridine: 2',5'-dideoxy-5-ethyl-5'-(4-nitrobenzamido)uridine, mp 250°–250.5° C.; and
(d) from 2-trifluoromethylbenzoyl chloride and 5'-amino-2',5'-dideoxy-5-ethyluridine: 2',5'-dideoxy-5-ethyl-5'-(2-trifluoromethylbenzamido)uridine, mp 263°–264° C.

EXAMPLE 3

(A) A solution of 1.12 g of (2,6-dichlorophenyl)acetyl chloride in 15 ml of diethyl ether was added to a solution of 1.275 g of 5'-amino-2',5'dideoxy-5-ethyluridine in 15 ml of 0.33M sodium hydroxide solution. The mixture was shaken vigorously for 10 minutes and then filtered. The solid was washed with 150 ml of water, 20 ml of ethanol and 40 ml of diethyl ether, and then recrystallized from 2.5 l of ethanol to give 1.53 g of 5'-[2-(2,6-dichlorophenyl)acetamido]-2',5'-dideoxy-5-ethyluridine in the form of a white solid of melting point 296°–297° C.

(B) In an analogous manner, there were obtained:
(a) from (2,6-dimethylphenyl)acetyl chloride and 5'-amino-2',5'-dideoxy-5-ethyluridine: 2',5'-dideoxy-5-ethyl-5'-[2-(2,6-dimethylphenyl)acetamido]uridine, mp 282° C.;
(b) from 2(RS)-(2-bromophenyl)propionyl chloride and 5'-amino-2',5'-dideoxy-5-ethyluridine: 5'-[2(RS)-(2-bromophenyl)propionamido]-2',5'-dideoxy-5-ethyluridine, mp 236°–236.5° C.;
(c) from 4-biphenylylacetyl chloride and 5'-amino-2',5'-dideoxy-5-ethyluridine: 5'-[2-(4-biphenylyl)acetamido]-2',5'-dideoxy-5-ethyluridine, mp 244° C.;
(d) from (2-chloro-3-nitrophenyl)acetyl chloride and 5'-amino-2',5'-dideoxy-5-ethyluridine: 5'-[2-(2-chloro-3-nitrophenyl)acetamido]-2',5'-dideoxy-5-ethyluridine, mp 240°–241.5° C.;
(e) from 2(RS)-(2,6-dichlorophenyl)propionyl chloride and 5'-amino-2',5'-dideoxy-5-ethyluridine: 5'-[2(RS)-(2,6-dichlorophenyl)propionamido]-2',5'-dideoxy-5-ethyluridine, mp 193°–194° C.;
(f) from (3,5-dimethylphenyl)acetyl chloride and 5'-amino-2',5'-dideoxy-5-ethyluridine: 2',5'-dideoxy-5-ethyl-5'-[2-(3,5-dimethylphenyl)acetamido]uridine, mp 234°–236° C.;
(g) from (3,5-dimethoxyphenyl)acetyl chloride and 5'-amino-2',5'-dideoxy-5-ethyluridine: 2',5'-dideoxy-5'-[2-(3,5-dimethoxyphenyl)acetamido]-5-ethyluridine, mp 219°–220.5° C.;
(h) from (2,3,5,6-tetramethylphenyl)acetyl chloride and 5'-amino-2',5'-dideoxy-5-ethyluridine: 2',5'-dideoxy-5-ethyl-5'-[2-(2,3,5,6-tetramethylphenyl)acetamido]uridine, mp 288° C.;
(i) from (2-bromophenyl)acetyl chloride and 5'-amino-2',5'-dideoxy-5-ethyluridine: 5'-[2-(2-bromophenyl)acetamido]-2',5'-dideoxy-5-ethyluridine, mp 247°–248° C.;
(j) from (2-methoxyphenyl)acetyl chloride and 5'-amino-2',5'-dideoxy-5-ethyluridine: 2',5'-dideoxy-5-ethyl-5'-[2-(2-methoxyphenyl)acetamido]uridine, mp 222°–224° C.;
(k) from (2-nitrophenyl)acetyl chloride and 5'-amino-2',5'-dideoxy-5-ethyluridine: 2',5'-dideoxy-5-ethyl-5'-[2-(2-nitrophenyl)acetamido]uridine, mp 240°–241° C.;
(l) from phenylacetyl chloride and 5'-amino-2',5'-dideoxy-5-ethyluridine: 2',5'-dideoxy-5-ethyl-5'-(2-phenylacetamido)uridine, mp 218°–219° C.; and
(m) from 2,6-dichlorophenylacetyl chloride and 5'-amino-5'-deoxythymidine: 5'-[2-(2,6-dichlorophenyl)acetamido]-5'-deoxythymidine, mp 276° C.

EXAMPLE 4

(A) A suspension of 108 mg of (2-bromophenyl)acetic acid and 1 ml of oxalyl chloride in 2.5 ml of benzene was stirred and 1 drop of dimethylformamide was added. The mixture was stirred at room temperature for 1.5 hours and then evaporated. The residue was taken up in 3 ml of diethyl ether and a solution of 153 mg of 5'-amino-5-bromo-2',5'-dideoxyuridine in 4.5 ml of 0.11M sodium hydroxide solution was added thereto. The mixture was shaken vigorously for 10 minutes and then filtered. The solid was recrystallized from ethanol to give 75 mg of 5-bromo-5'-[2-(2-bromophenyl)acetamido]-2',5'-dideoxyuridine in the form of a white solid of melting point 222°–223° C.

(B) In an analogous manner, there were obtained:
(a) from 2(RS)-(2,4-dichlorophenoxy)propionic acid and 5'-amino-5-bromo-2',5'-dideoxyuridine: 5-bromo-5'-[2(RS)-(2,4-dichlorophenoxy)propionamido]-2',5'-dideoxyuridine, mp 171°–172° C.;
(b) from 2,6-dichlorophenylacetic acid and 5'-amino-5-bromo-2',5'-dideoxyuridine: 5-bromo-5'-[2-(2,6-dichlorophenyl)acetamido]-2',5'-dideoxyuridine, mp 232°–233° C.;
(c) from benzoic acid and 5'-amino-5-bromo-2',5'-dideoxyuridine: 5'-benzamido-5-bromo-2',5'-dideoxyuridine, mp 221°–222° C.;
(d) from 2(RS)-(2,4-dichlorophenoxy)propionic acid and 5'-amino-2',5'-dideoxy-5-iodouridine: 5'-[2(RS)-(2,4-dichlorophenoxy)propionamido]-2',5'-dideoxy-5-iodouridine, mp 205°–207° C.;
(e) from 2(RS)-(2,4,5-trichlorophenoxy)propionic acid and 5'-amino-2',5'-dideoxy-5-iodouridine: 5'-[2(RS)-2,4,5-trichlorophenoxy)propionamido]-2',5'-dideoxy-5-iodouridine, mp 214°–215° C.; and
(f) from 2,6-dichlorophenylacetic acid and 5'-amino-2',5'-dideoxy-5-iodouridine: 5'-[2-(2,6-dichlorophenyl)acetamido]-2',5'-dideoxy-5-iodouridine, mp 225° C.

EXAMPLE 5

0.84 ml of a 1M sodium hydroxide solution was added to a solution of 256 mg of 5'-amino-5-bromo-2',5'-dideoxycytidine in 3.3 ml of water. A solution of (2-bromophenyl)acetyl chloride (prepared from 185 mg of the acid) in 5 ml of dichloromethane was added, the mixture was shaken vigorously for 10 minutes and then filtered. The solid was recrystallized from 30 ml of ethanol to give 44 mg of 5-bromo-5'-[2-(2-bromophenyl)acetamido]-2',5'-dideoxycytidine in the form of a white solid of melting point 164°–167° C.

The 5'-amino-5-bromo-2',5'-dideoxycytidine used as the starting material was prepared as follows:

A solution of 3.06 g of 5-bromo-2'-deoxycytidine and 2.3 g of p-toluenesulfonyl chloride in 50 ml of pyridine was stirred at 4° C. for 24 hours. An additional 1.91 g of p-toluenesulfonyl chloride were added and stirring was continued at 4° C. for an additional 22 hours. 20 ml of methanol were added, the mixture was stirred at room temperature for 30 minutes and then evaporated. The crude product was subjected to flash chromatography on a column of silica gel using ethyl acetate/methanol (9:1) for the elution, there being obtained 2.26 g of 5-bromo-2'-deoxy-5'-O-p-toluenesulfonylcytidine in the form of a white solid of melting point 168° C. (decomposition).

A solution of 2.19 g of the above solid and 354 mg of lithium azide in 26 ml of dimethylformamide was stirred at 75° C. for 2 hours. The solvent was removed by evaporation and the residue was triturated with diethyl ether to give 1.351 g of 5'-azido-5-bromo-2',5'-dideoxycytidine in the form of a white solid of melting point 192°–193° C. (decomposition).

A solution of 1.30 g of the above solid and 1.648 g of triphenylphosphine in 50 ml of pyridine was stirred at room temperature for 100 minutes. 5 ml of ammonium hydroxide solution were added, the mixture was stirred for an additional 3 hours and then evaporated. The residue was washed four times with 40 ml of toluene each time and four times with 40 ml of diethyl ether each time, and then extracted twice with 125 ml of water each time. The combined aqueous extracts were evaporated, the residue was dissolved in 25 ml of ethanol and the solution was diluted with 300 ml of diethyl ether, whereby a white solid precipitated. After standing at 0° C. overnight, the solid was collected by filtration to give 0.53 g of 5'-amino-5-bromo-2',5'-dideoxycytidine in the form of a white powder which decomposed above 115° C.

EXAMPLE 6

(A) A mixture of 400 mg of 5'-[2-(2,6-dichlorophenyl)acetamido]-2',5'-dideoxy-5-ethyluridine, 0.15 ml of butyryl chloride and 1 mg of 4-dimethylaminopyridine in 50 ml of pyridine was stored at room temperature overnight and then evaporated. The residue was subjected to flash chromatography on a column of silica gel using dichloromethane/methanol (24:1) for the elution, there being obtained 175 mg of 3'-O-butyryl-5'-[2-(2,6-dichlorophenyl)acetamido]-2',5'-dideoxy-5-ethyluridine in the form of a white solid of melting point 130°–132° C.

(B) In an analogous manner, there were obtained:
(a) from 5'-[2-(2,6-dichlorophenyl)acetamido]-2',5'-dideoxy-5-ethyluridine and 3,3-dimethylbutyryl chloride:
2',5'-dideoxy-5'-[2-(2,6-dichlorophenyl)acetamido]-3'-O-(3,3-dimethylbutyryl)-5-ethyluridine, mp 77°–79° C.;
(b) from 5'-[2-(2,6-dichlorophenyl)acetamido]-2',5'-dideoxy-5-ethyluridine and palmitoyl chloride:
5'-[2-(2,6-dichlorophenyl)acetamido]-2',5'-dideoxy-5-ethyl-3'-O-palmitoyluridine, mp 150° C.; and
(c) from 5'-[2-(2,6-dichlorophenyl)acetamido]-2',5'-dideoxy-5-ethyluridine and acetyl chloride:
3'-O-acetyl-5'-[2-(2,6-dichlorophenyl)acetamido]-2',5'-dideoxy-5-ethyluridine, mp 193°–194° C.

EXAMPLE 7

(A) A solution of (2,6-dichlorophenyl)acetyl chloride (prepared from 103 mg of the acid) in 2 ml of diethyl ether was added to a solution of 173 mg of 5'-amino-3'-O-benzyl-2',5'-dideoxy-5-ethyluridine in 4.5 ml of 0.11M sodium hydroxide solution. The mixture was shaken vigorously for 10 minutes and then filtered. The solid was recrystallized from ethanol to give 120 mg of 3'-O-benzyl-5'-[2-(2,6-dichlorophenyl)acetamido]-2',5'-dideoxy-5-ethyluridine in the form of a white solid of melting point 174°–177° C.

(B) In an analogous manner, from 2(RS)-(2,4-dichlorophenoxy)propionic acid and 5'-amino-3'-O-benzyl-2',5'-dideoxy-5-ethyluridine there was obtained 3'-O-benzyl-5'-[2(RS)-(2,4-dichlorophenoxy)propionamido]-2',5'-dideoxy-5-ethyluridine of melting point 195°–200° C.

The 5'-amino-3'-O-benzyl-2',5'-dideoxy-5-ethyluridine used above as the starting material was prepared as follows:

A mixture of 6.5 g of 2'-deoxy-5-ethyl-5'-O-trityluridine, 19 g of powdered potassium hydroxide and 9.5 ml of benzyl chloride in a mixture of 60 ml of benzene and 21 ml of dioxane was stirred and heated under reflux for 4 hours. After cooling 65 ml of water and 20 ml of acetic acid were added and the phases were separated. The organic phase was washed twice with 90 ml of water each time, dried over anhydrous sodium sulfate and evaporated to give 4.5 g of 3'-O-benzyl-2'-deoxy-5-ethyl-5'-O-trityluridine in the form of a sticky solid.

A solution of the above product in a mixture of 32 ml of acetic acid and 8 ml of water was stirred and heated under reflux for 10 minutes. The mixture was cooled to 0° C. and filtered. The filtrate was triturated with 100 ml of water to give a sticky solid. This was subjected to flash chromatography on a column of silica gel using ethyl acetate for the elution. The product was crystallized from a mixture of acetone and petroleum ether (boiling point 60°–80° C.) to give 1.25 g of 3'-O-benzyl-2'-deoxy-5-ethyluridine in the form of a colorless glass-like solid.

A mixture of 1.2 g of the above product, 929 mg of triphenylphosphine, 1.131 g of sodium azide and 1.179 g of carbon tetrabromide in 14 ml of dimethylformamide was stirred at room temperature for 20 hours. 8 ml of methanol were added, the mixture was stirred for 30 minutes and then evaporated. The residue was suspended in 80 ml of water and extracted three times with 60 ml of ethyl acetate each time. The combined ethyl acetate extracts were washed with water, dried over anhydrous sodium sulfate and evaporated. The residue was subjected to flash chromatography on a column of silica gel using ethyl acetate acetate/hexane (2:1) for the elution, there being obtained 1.20 g of 5'-azido-3'-O-benzyl-2',5'-dideoxy-5-ethyluridine in the form of a colorless gum.

A solution of 1.40 g of the above product and 1.582 g of triphenylphosphine in 48 ml of pyridine was stirred at room temperature for 100 minutes. 5 ml of ammonium hydroxide solution were added, the mixture was stirred at room temperature for an additional 3 hours and then evaporated to dryness. The residue was crystallized from a mixture of ethyl acetate and hexane to give a pale grey solid. This solid was suspended in 30 ml of diethyl ether, the suspension was stirred for 1.5 hours and then filtered to give 0.45 g of 5'-amino-3'-O-benzyl-2',5'-dideoxy-5-ethyluridine in the form of a white solid of melting point 95° C. (decomposition).

EXAMPLE 8

(A) A solution of (2,6-dichlorophenyl)acetyl chloride (prepared from 103 mg of the acid) in 2 ml of diethyl ether was added to a solution of 140 mg of 5'-amino-2',5'-dideoxy-3'-O-ethyl-5-ethyluridine in 2.5 ml of 0.2M sodium hydroxide solution, the mixture was shaken vigorously for 10 minutes and then filtered. The solid was washed with 5 ml of water and 50 ml of diethyl ether, and then recrystallized from acetone to give 60 mg of 5'-[2-(2,6-dichlorophenyl)acetamido]-2',5'-dideoxy-3'-O-ethyl-5-ethyluridine in the form of a white solid of melting point 249°–250° C.

(B) In an analogous manner, from 2(RS)-(2,4-dichlorophenoxy)propionyl chloride (prepared from the acid) and 5'-amino-2',5'-dideoxy-3'-O-ethyl-5-ethyluridine, there was obtained 5'-[2(RS)-(2,4-dichlorophenoxy)propionamido]-2',5'-dideoxy-3'-O-ethyl-5-ethyluridine of melting point 121°–124° C.

The 5'-amino-2',5'-dideoxy-3'-O-ethyl-5-ethyluridine used above as the starting material was prepared as follows:

A mixture of 6 g of 2'-deoxy-5-ethyl-5'-O-trityluridine, 1.347 g of powdered potassium hydroxide and 1.95 ml of ethyl iodide in a mixture of 60 ml of benzene and 20 ml of dioxane was stirred and heated under reflux for 14 hours. The solvents were removed by evaporation, the residue was taken up in 6 ml of methanol and the solution was poured into 250 ml of water. The resulting mixture was extracted four times with 150 ml of chloroform each time and the combined chloroform extracts were evaporated to give 2'-deoxy-3'-O-ethyl-5-ethyl-5'-O-trityluridine which was used directly in the next step.

A solution of the above product in a mixture of 52 ml of acetic acid and 13 ml of water was stirred and heated under reflux for 1 hour and then evaporated to dryness. The residue was subjected to flash chromatography on a column of silica gel using ethyl acetate for the elution, there being obtained 1.57 g of 2'-deoxy-3'-O-ethyl-5-ethyluridine in the form of a white solid of melting point 157° C.

A mixture of 1.40 g of 2'-deoxy-3'-O-ethyl-5-ethyluridine, 1.3 g of triphenylphosphine, 1.59 g of sodium azide and 1.66 g of carbon tetrabromide in 19 ml of dimethylformamide was stirred at room temperature for 20 hours. 11 ml of methanol were added, the mixture was stirred for 30 minutes and then evaporated. The residue was suspended in 110 ml of water and extracted three times with 70 ml of ethyl acetate each time. The combined ethyl acetate extracts were evaporated and the residue was subject to flash chromatography on a column of silica gel using ethyl acetate/hexane (2:1) for the elution, there being obtained 1.26 g of 5'-azido-2',5'-dideoxy-3'-O-ethyl-5-ethyluridine in the form of a colorless oil.

A solution of 1.26 g of the above oil in 100 ml of methanol was hydrogenated over 10% palladium-on-carbon catalyst at room temperature and under atmospheric pressure for 4.5 hours. The catalyst was removed by filtration and the filtrate was evaporated. The residue was recrystallized from a mixture of ethyl acetate and hexane to yield 780 mg of 5'-amino-2',5'-dideoxy-3'-O-ethyl-5-ethyluridine in the form of a white solid of melting point 122°-123° C.

EXAMPLE 9

A solution of 210 mg of (2-bromophenyl)acetyl chloride in 3 ml of diethyl ether was added to a solution of 324 mg of 5'-amino-4-N-benzoyl-2',5'-dideoxy-5-ethylcytidine in 4.9 ml of 0.18M sodium hydroxide solution and the mixture was shaken vigorously for 10 minutes. The solid was collected by filtration, washed with 2 ml of water and 1 ml of diethyl ether and recrystallized from 15 ml of ethanol to give 100 mg of 4-N-benzoyl-5'-[2-(2-bromophenyl)acetamido]-2',5'-dideoxy-5-ethylcytidine in the form of a white solid which was processed further without purification.

A solution of 100 mg of the above solid in 20 ml of methanolic ammonia solution was stored at room temperature overnight. It was then evaporated to dryness and the residue was triturated with 20 ml of diethyl ether to give 52 mg of 5'-[2-(2-bromophenyl)acetamido]-2',5'-dideoxy-5-ethylcytidine in form of a white solid of melting point 236°-237° C.

The 5'-amino-4-N-benzoyl-2',5'-dideoxy-5-ethylcytidine used as the starting material was prepared as follows:

A solution of 4.08 g of 2'-deoxy-5-ethylcytidine in 200 ml of ethanol was stirred and heated under reflux. 3.94 g of benzoic anhydride were added and additional portions, each of 3.94 g, of benzoic anhydride were added after 1, 2 and 4 hours. The mixture was heated under reflux for an additional 1 hour after the final addition and was then evaporated to dryness. The residue was suspended in 250 ml of diethyl ether and stored at room temperature overnight. The solid was collected by filtration and washed with 75 ml of diethyl ether to give 4.5 g of 4-N-benzoyl-2'-deoxy-5-ethylcytidine in the form of a white solid of melting point 172°-174° C.

A mixture of 1.436 g of N-benzoyl-2'-deoxy-5-ethylcytidine, 1.072 g of triphenylphosphine, 1.304 g of sodium azide and 1.360 g of carbon tetrabromide in 16 ml of dimethylformamide was stirred at room temperature for 20 hours. 8 ml of methanol were added, the mixture was stirred for 30 minutes and then evaporated. The residue was suspended in 80 ml of water and extracted three times with 100 ml of ethyl acetate each time. The combined ethyl acetate extracts were washed with water and evaporated. The residue was subjected to flash chromatography on a column of silica gel using ethyl acetate for the elution, there being obtained 1 g of 5'-azido-4-N-benzoyl-2',5'-dideoxy-5-ethylcytidine in the form of a white crystalline solid of melting point 125°-126° C.

A solution of 500 mg of the above product in 30 ml of methanol was hydrogenated over 10% palladium-on-carbon catalyst at room temperature and under atmospheric pressure for 4 hours. The catalyst was removed by filtration and the filtrate was evaporated to yield 5'-amino-4-N-benzoyl-2',5'-dideoxy-5-ethylcytidine in the form of a colorless gum.

EXAMPLE 10

A solution of (2,6-dichlorophenyl)acetyl chloride (prepared from 146 mg of the acid) in 1 ml of diethyl ether was added to a solution of 170 mg of 5'-amino-2',3',5'-trideoxy-5-ethyluridine in 2.72 ml of 0.26M sodium hydroxide solution and the mixture was shaken for 10 minutes. The mixture was filtered and the solid was recrystallized from 20 ml of ethanol to give 150 mg of 2',3',5'-trideoxy-5'-[2-(2,6-dichlorophenyl)acetamido]-5-ethyluridine in the form of a white solid of melting point 237°-238° C.

The 5'-amino-2',3',5'-trideoxy-5-ethyluridine used as the starting material was prepared as follows:

A solution of 16.0 g of 2'-deoxy-5-ethyl-5'-O-trityluridine and 6.8 ml of methanesulfonyl chloride in 140 ml of pyridine was stored at 0° C. overnight. 3 g of ice were added, the mixture was stored at 0° C. for 1 hour and then poured into 1500 ml ice/water. The resulting solid was collected by filtration, washed with 500 ml of water and dried to yield 17.35 g of 2'-deoxy-5-ethyl-3'-O-methanesulfonyl-5'-O-trityluridine in the form of a white solid which was used in the next step without further purification.

A mixture of 1.2 g of the above product and 681 mg of sodium iodide in 10 ml of ethyl methyl ketone was stirred and heated under reflux for 7 hours. The mixture was allowed to cool and was then filtered. The filtrate was evaporated to give a colorless gum which was subjected to flash chromatography on a column of silica gel using ethyl acetate/hexane (2:1) for the elution. The product was crystallized from a mixture of ethyl acetate and hexane to give 360 mg of 2',3'-dideoxy-5-ethyl-3'- iodo-5'-O-trityluridine in the form of white crystals of melting point 93°–98° C.

A solution of 720 mg of 2',3'-dideoxy-5-ethyl-3'-iodo-5'-O-trityluridine in a mixture of 16 ml of acetic acid and 4 ml of water was stirred and heated under reflux for 1 hour. The solvent was removed by evaporation and the residue was crystallized from a mixture of ethyl acetate and hexane to give 180 mg of 2',3'-dideoxy-5-ethyl-3'-iodouridine in the form of a white solid of melting point 161.5°–163° C.

A solution of 2.50 g of 2',3'-dideoxy-5-ethyl-3'-iodouridine in a mixture of 90 ml of ethanolic ammonia and 17 ml of water was hydrogenated over 5% palladium on barium sulfate catalyst at room temperature and under atmospheric pressure for 3 hours. The mixture was filtered and the filtrate was evaporated. The residue was extracted twice with 250 ml of hot ethyl acetate each time and the combined ethyl acetate extracts were evaporated. The residue was chromatographed on a short column of silica gel using ethyl acetate for the elution and the product was crystallized from a mixture of ethyl acetate and hexane to give 1.17 g of 2',3'-dideoxy-5-ethyluridine in the form of a white solid of melting point 109°–113° C.

A mixture of 350 mg of 2',3'-dideoxy-5-ethyluridine, 391 mg of triphenylphosphine, 475 mg of sodium azide and 496 mg of carbon tetrabromide was stirred at room temperature for 20 hours. 3 ml of methanol were added, the mixture was stirred for 1 hour and then evaporated. The residue was suspended in 30 ml of water and extracted twice with 50 ml of ethyl acetate each time. The combined ethyl acetate extracts were washed with 20 ml of water and then evaporated. The residue was subjected to flash chromatography on a column of silica gel using ethyl acetate for the elution. The product was crystallized from a mixture of ethyl acetate and hexane to give 200 mg of 5'-azido-2',3',5'-trideoxy-5-ethyluridine in the form of a white solid which was processed directly without further purification.

A solution of 190 mg of the above product in 25 ml of methanol was hydrogenated over 100 mg of 10% palladium-on-carbon catalyst at room temperature and under atmospheric pressure for 4 hours. The catalyst was removed by filtration and the filtrate was evaporated to give 180 mg of 5'-amino-2',3',5'-trideoxy-5-ethyluridine in the form of a colorless gum.

EXAMPLE 11

A solution of 0.2 g of 2',5'-dideoxy-5-ethyl-5'-[2-(2-nitrophenyl)acetamido]uridine in 100 ml of ethanol was hydrogenated over 0.1 g of 10% palladium-on-carbon catalyst at room temperature and under atmospheric pressure until the uptake of hydrogen was complete. The mixture was filtered and the filtrate was evaporated to yield an oil which crystallized from ethanol to give 0.1 g of 5'-[2-(2-aminophenyl)acetamido]-2',5'-dideoxy-5-ethyluridine in the form of a white solid of melting point 195°–196° C.

EXAMPLE 12

A solution of 0.2 g of 5'-[2-(2-aminophenyl)acetamido]-2',5'-dideoxy-5-ethyluridine in 5 ml of dry pyridine was treated with 0.5 g of acetic anhydride and the mixture was stored at room temperature for 17 hours. The mixture was then evaporated to give an oil which crystallized from ethanol to yield 0.13 g of 5'-[2-(2-acetamidophenyl)acetamido]-3'-O-acetyl-2',5'-dideoxy-5-ethyluridine in the form of a buff colored solid of melting point 143°–145° C.

EXAMPLE 13

A solution of 0.2 g of 5'-[2-(2-acetamidophenyl)acetamido]-3'-O-acetyl-2',5'-dideoxy-5-ethyluridine in 20 ml of methanol was treated with 20 ml of methanol saturated with ammonia. The mixture was left to stand at room temperature for 17 hours. A white solid separated and was collected by filtration, washed twice with 5 ml of ethanol each time and twice with 5 ml of diethyl ether each time and subsequently dried to give 5'-[2-(2-acetamidophenyl)acetamido]-2',5'-dideoxy-5-ethyluridine of melting point 266°–267° C.

EXAMPLE 14

In a manner analogous to that described in Example 1, there were obtained:
(a) from 5'-amino-5'-deoxythymidine and (2-bromophenyl)acetyl chloride:
5'-[2-(2-bromophenyl)acetamido]-5'-deoxythymidine, mp 232°–233° C.;
(b) from 5'-amino-5'-deoxythymidine and (4-nitrophenyl)acetyl chloride:
5'-deoxy-5'-[2-(4-nitrophenyl)acetamido]thymidine, mp 240°–241° C.;
(c) from 5'-amino-5'-deoxythymidine and phenylacetyl chloride:
5'-deoxy-5'-(2-phenylacetamido)thymidine, mp 221°–222° C.; and
(d) from 5'-amino-5'-deoxythymidine and (4-trifluoromethylphenyl)acetyl chloride:
5'-deoxy-5'-[2-(4-trifluoromethylphenyl)acetamido]thymidine, mp 252°–253° C.

EXAMPLE 15

0.2 g of (4-hydroxy-2,6-dimethylphenyl)acetic acid in 10 ml of benzene was treated with 0.15 g of oxalyl chloride and 1 drop of dimethylformamide and the mixture was stirred for 2 hours. The solvent was removed by evaporation, the residue was cooled −20° C. and then dissolved in 6 ml of dry pyridine. 0.26 g of 5'-amino-2',5'-dideoxy-5-ethyluridine was added and the mixture was stirred at 0° C. for 4 hours and then left to stand at 4° C. overnight. The solvent was removed by evaporation and the residue was re-evaporated with toluene and water. The residue was triturated with water at 0° C. and the resulting solid was removed by filtration and dried in vacuo to give 0.175 g of crude product of melting point 232°–238° C. (decomposition). Recrystallization from 6 ml of methanol gave 0.06 g of pure 2',5'-dideoxy-5-ethyl-5'-[2-(4-hydroxy-2,6-dimethylphenyl)acetamido]uridine of melting point 240°–243° C. (decomposition).

EXAMPLE 16

0.32 g of 5'-amino-5-(2-chloroethyl)-2',5'-dideoxyuridine hydrochloride were dissolved in a mixture of 5 ml of water and 2.5 ml of 1M sodium hydroxide solution. The mixture was shaken vigorously for 25 minutes with a benzene solution of (2,6-dichlorophenyl)acetyl chloride (prepared from 0.22 g of the acid by treatment with oxalyl chloride). The resulting solid was removed by filtration and washed with water and then with diethyl ether to give 0.29 g of crude product of melting point 248°–249° C. (decomposition). 0.1 g of this solid was stirred successively for 1 hour each time with 1 ml of water, 2 ml of ethanol and 2 ml of methanol to give 0.03 g of 5-(2-chloroethyl)-5′-[2-(2,6-dichlorophenyl)-acetamido]-2′,5′-dideoxyuridine of melting point 253°–254° C. (decomposition).

The 5′-amino-5-(2-chloroethyl)-2′,5′-dideoxyuridine hydrochloride used as the starting material was prepared as follows:

1.4 g of 5-(2-chloroethyl)-2′-deoxyuridine and 1.3 g of triphenylphosphine were dissolved in 20 ml of dimethylformamide and stirred while 1.2 g of lithium azide were added to give a solution within 5 minutes at room temperature. 1.7 g of carbon tetrabromide were added portionwise during 5 minutes to give a hazy orange colored solution which was stirred at room temperature for 17 hours. 5 ml of methanol were added to give a clear solution. After 0.5 hour, the solvents were removed by evaporation under an oil pump vacuum to give a gum which was partitioned between 30 ml of ethyl acetate and 20 ml of water. The white solid which formed was removed by filtration to give 0.64 g of crude product of melting point 179°–182° C. (decomposition). This crude product was stirred with methanol and then removed by filtration to give 0.48 g of pure 5′-azido-2′,5′-dideoxy-5-(2-chloroethyl)-uridine of melting point 197°–199° C. (decomposition).

0.16 g of 5′-azido-2′,5′-dideoxy-5-(2-chloroethyl)uridine was dissolved in 100 ml of methanol and 1.9 ml of a 0.27M solution of hydrogen chloride in methanol was added. A slurry of 25 mg of 5% palladium-on-charcoal catalyst in 10 ml of ethanol was added under a nitrogen atmosphere and the mixture was hydrogenated at room temperature and under atmospheric pressure for 2 hours. The catalyst was removed by filtration and the filtrate was evaporated to give a solid which, after crystallization from a mixture of 15 ml of methanol and 30 ml of diethyl ether, gave 0.13 g of 5′-amino-5-(2-chloroethyl)-2′,5′-dideoxyuridine hydrochloride melting point 229°–230° C. (decomposition).

EXAMPLE 17

0.72 g of 2′,5′-dideoxy-5-ethyl-5′-methylaminouridine in 25 ml of dry pyridine was stirred at 0° C. and treated with a solution of (2-bromophenyl)acetyl chloride (prepared from 0.65 g of the acid by treatment with thionyl chloride in benzene under reflux) in 7 ml of benzene. The mixture was stirred at 0° C. for 0.5 hour and then stored at 4° C. overnight. The solvents were removed by evaporation and the residue was re-evaporated with toluene to give a gum which was subsequently triturated with diethyl ether to yield a solid. This solid was taken up in 5 ml of methylene chloride/methanol (9:1) and chromatographed on a column of silica gel using methylene chloride/methanol (9:1) for the elution. The fractions containing the product were combined and evaporated. The residue was re-evaporated with ethanol and recrystallized from methanol to give 0.18 g of 5′-[2-(2-bromophenyl)-N-methylacetamido]-2′,5′-dideoxy-5-ethyluridine of melting point 182°–185° C.

In an analogous manner, from (2(RS)-(2,4-dichlorophenoxy)propionyl chloride and 2′,5′-dideoxy-5-ethyl-5′-methylaminouridine there was obtained 5′-[2(RS)-(2,4-dichlorophenoxy)-N-methylpropionamido]-2′, 5′-dideoxy-5-ethyluridine of melting point 167°–177° C. (decomposition).

The 2′,5′-dideoxy-5-ethyl-5′-methylaminouridine used above as the starting material was prepared as follows:

26 g of 2′-deoxy-5-ethyluridine were dissolved in 400 ml of dry pyridine. The solution was cooled to 0° C. and stirred while 20 g of p-toluenesulfonyl chloride were added portionwise. Stirring at 0° C. was continued for 1 hour and the mixture was then left to stand at 4° C. overnight. The solvent was removed by evaporation and the residue was re-evaporated with toluene. The residue was shaken with 200 ml of methanol and left to stand in a refrigerator for 2.5 hours to give a solid which was removed by filtration, washed with methanol and dried in vacuo to give 18 g of crude product of melting point 183° C. (decomposition). Recrystallization from 450 ml of ethanol gave 13 g of pure 2′-deoxy-5-ethyl-5′-O-(p-toluenesulfonyl)uridine of melting point 189°–190° C. (decomposition).

1.8 g of the above product was dissolved in 10 ml of dry dimethylformamide and 1.2 ml of N-benzylmethylamine were added. The mixture was stirred under nitrogen and heated at 80° C. for 5 hours. The solvent was removed by evaporation and the residue was re-evaporated with toluene. The residue was triturated with diethyl ether and removed by filtration to give 2.6 g of a solid of melting point 110°–115° C. This solid was taken up in 10 ml of methylene chloride/methanol (9:1) and chromatographed on a column of silica gel using methylene chloride/methanol (9:1) for the elution. The fractions containing the product were combined and evaporated. The residue was triturated with diethyl ether to give 1.2 g of 2′,5′-dideoxy-5-ethyl-5′-(N-methyl-N-benzylamino)uridine of melting point 135°–137° C.

1.1 g of 2′,5′-dideoxy-5-ethyl-5′-(N-methyl-N-benzylamino)uridine were taken up in 75 ml of ethanol and 1 g of 5% palladium-on-carbon catalyst in 25 ml of ethanol was added under a nitrogen atmosphere. The mixture was hydrogenated at room temperature and under atmospheric pressure. The catalyst was removed by filtration and the filtrate was evaporated to give 0.84 g of 2′,5′-dideoxy-5-ethyl-5′-methylaminouridine of melting point 145°–147° C.

EXAMPLE 18

In a manner analogous to that described in Example 17, there was obtained:

(a) from (2,6-dichlorophenyl)acetyl chloride (prepared from 0.29 g of the acid by treatment with oxalyl chloride) and 0.35 g of 2′,5′-dideoxy-5-ethyl-5′-methylaminouridine there was obtained, after chromatography and recrystallization from a mixture of 8 ml of ethanol and 24 ml of diethyl ether, 0.19 g of 5′-[2-(2,6-dichlorophenyl)-N-methylacetamido]-2′,5′-dideoxy-5-ethyluridine of melting point 209°–210° C.

(b) from 2(RS)-(2-bromophenyl)propionyl chloride (prepared from 0.32 g of the acid by treatment with oxalyl chloride) and 0.35 g of 2′,5′-dideoxy-5-ethyl-5′-methylaminouridine there was obtained, after chromatography on silica gel using methylene chloride/methanol (9:1) for the elution, 0.19 g of 5′-[2(RS)-(2-bromophenyl)-N-methylpropionamido]-2′,5′-dideoxy-5-ethyluridine of melting point 80°–90° C. (decomposition).

EXAMPLE 19

0.05 g of 5′-[2-(2-bromophenyl)-N-methylacetamido]-2′,5′-dideoxy-5-ethyluridine was dissolved in 2 ml of dry pyridine and the solution was treated with 0.12 ml of acetic anhydride. The mixture was stirred at room temperature for 5 hours and then evaporated. The residue was re-evaporated with toluene to give a solid which was triturated with diethyl ether and then removed by filtration. There was obtained 0.03 g of 3′-O-acetyl-5′-

[2-(2-bromophenyl)-N-methylacet-amido]-2',5'-dideoxy-5-ethyluridine of melting point about 170° C.

EXAMPLE 20

(A) 1.2 ml of a 1M sodium hydroxide solution was added to 0.255 g of 5'-amino-2',5'-dideoxy-5-ethyluridine in 5 ml of water and then 0.21 g of naphthaloyl chloride was added. The mixture was shaken vigorously for 10 minutes, whereby a white solid separated. This solid was collected by filtration, washed three times with 5 ml of water each time and then dried in vacuo. Recrystallization from ethanol gave 0.2 g of 2',5'-dideoxy-5-ethyl-5'-(2-naphthalamido)uridine in the form of a white solid of melting point 242°–244° C.

(B) In an analogous manner, there were prepared:
(a) from 5'-amino-2',5'-dideoxy-5-ethyluridine and 2-phenylbenzoyl chloride:
2',5'-dideoxy-5-ethyl-5'-(2-phenylbenzamido)uridine, mp 246°–247° C.;
(b) from 5'-amino-2',5'-dideoxy-5-ethyluridine and 3-phenylpropionyl chloride:
2',5'-dideoxy-5-ethyl-5'-(3-phenylpropionamido)uridine, mp 225°–226° C.;
(c) from 5'-amino-2',5'-dideoxy-5-ethyluridine and 4-phenylbutyryl chloride:
2',5'-dideoxy-5-ethyl-5'-(4-phenylbutyramido)uridine, mp 215° C.;
(d) from 5'-amino-2',5'-dideoxy-5-ethyluridine and cinnamoyl chloride:
2',5'-dideoxy-5'-cinnamamido-5-ethyluridine, mp 252°–254° C.;
(e) from 5'-amino-2',5'-dideoxy-5-ethyluridine and phenylpropiolyl chloride:
2',5'-dideoxy-5-ethyl-5'-(3-phenyl-2-propynamido)uridine, mp 234°–236° C.;
(f) from 5'-amino-2',5'-dideoxy-5-ethyluridine and 3-(phenylsulfonyl)propionyl chloride:
2',5'-dideoxy-5-ethyl-5'-[3-(phenylsulfonyl)propionamido]uridine, mp 190°–192° C.; and
(g) from 5'-amino-2',5'-dideoxy-5-ethyluridine and 2-bromocinnamoyl chloride:
5'-(2-bromocinnamamido)-2',5'-dideoxy-5-ethyluridine, mp 202°–204° C.

EXAMPLE 21

(A) 5 g of oxalyl chloride were added to a mixture of 5 g of 2-thiopheneacetic acid and 1 drop of dimethylformamide in 40 ml of dry benzene. After stirring for 2 hours, the benzene was removed by evaporation and the crude 2-thiopheneacetyl chloride was purified by distillation.

0.18 g of 2-thiopheneacetyl chloride was added to a solution of 0.255 g of 5'-amino-2',5'-dideoxy-5-ethyluridine in 5 ml of water containing 1.2 of 1M sodium hydroxide solution and the resulting mixture was shaken vigorously for 10 minutes. The resulting white solid was collected by filtration, washed with water, dried at 50° C. in vacuo over phosphorus pentoxide and recrystallized from ethanol to give 0.2 g of 2',5'-dideoxy-5-ethyl-5'-[2-(2-thienyl)acetamido]ridine of melting point 215°–217° C.

(B) In an analogous manner, there were obtained:
(a) from 5'-amino-2',5'-dideoxy-5-ethyluridine and 3-thiopheneacetic:
2',5'-dideoxy-5-ethyl-5'-[2-(3-thienyl)acetamido]uridine, mp 220°–222° C; and
(b) from 5'-amino-2',5'-dideoxy-5-ethyluridine and 1-adamantanecarbonyl chloride:
5'-(1-adamantylcarboxamido)-2',5'-dideoxy-5-ethyluridine, mp 160°–162° C.

EXAMPLE 22

(A) A solution of 0.255 g of 5'-amino-2',5'-dideoxy-5-ethyluridine in a mixture of 5 ml of water and 1.1 ml of 1M sodium hydroxide solution was treated with 0.14 g of picolinoyl chloride. The reaction mixture was shaken vigorously for 15 minutes and the resulting dark brown solution was extracted twice with 10 ml of n-butanol each time. The extracts were washed with saturated sodium chloride solution, dried over anhydrous sodium sulfate and evaporated to give a buff colored solid. The solid was purified by flash chromatography on a column of silica gel using ethyl acetate for the elution. Fractions containing the product were combined and evaporated to give a light brown solid. Recrystallization from ethanol/diethyl ether gave 0.12 g of 2',5'-dideoxy-5-ethyl-5'-(2-pyridylcarboxamido)uridine in the form of a white solid of melting point 196°–198° C.

(B) In an analogous manner, from 5'-amino-2',5'-dideoxy-5-ethyluridine and nicotinoyl chloride there was obtained 2',5'-dideoxy-5-ethyl-5'-(3-pyridylcarboxamido)uridine of melting point 223°–225° C.

EXAMPLE 23

A mixture of 0.26 g of 5'-amino-2',5'-dideoxy-5-ethyluridine 0.2 g of phenylsulfonylacetic acid and 1.2 g of dicyclohexylcarbodiimide in 10 ml of dry pyridine was stirred overnight at room temperature. The solvent was removed by evaporation and the residue was re-evaporated three times with toluene and twice with diethyl ether. The residue was triturated with diethyl ether and left to stand at room temperature. The resulting solid was removed by filtration, washed with diethyl ether and dried in vacuo. The solid (0.66 g) was recrystallized from 15 ml of ethanol to give 0.40 g of product of melting point 213°–217° C. Further recrystallization of 0.2 g of this product from 15 ml of ethanol gave 0.09 g of 2',5'-dideoxy-5-ethyl-5'-[2-(phenylsulfonyl)acetamido]uridine in the form of a white solid of melting point 218°–219° C.

EXAMPLE 24

0.23 g of 9-fluorenecarboxylic acid was stirred in 10 ml of benzene at 25° C. and treated with 0.15 g of oxalyl chloride and 1 drop of dimethylformamide. The mixture was left to stand for 1.5 hours and was then evaporated. The residue was dissolved in 1.5 ml of benzene and added to a solution of 0.26 g of 5'-amino-2',5'-dideoxy-5-ethyluridine in 5 ml of water and 1.5 ml of 1M sodium hydroxide solution. The mixture was shaken vigorously for 15 minutes and then evaporated partially. The resulting solid was removed by filtration and washed successively with water, ethanol and diethyl ether to give 0.22 g of 2',5'-dideoxy-5-ethyl-5'-(9-fluorenylcarboxamido)uridine of melting point 275°–278° C. (decomposition).

EXAMPLE 25

A slurry of 0.45 g of 2',5'-dideoxy-5-ethyl-5'-(9-fluorenylcarboxamido)uridine in 9 ml of dry pyridine was stirred and treated with 0.6 ml of acetic anhydride. The mixture was stirred at room temperature for 4 hours and then left to stand overnight. The solvent was removed by evaporation and the residue was re-evaporated with toluene. The residue was triturated with diethyl ether to give 0.4 g of crude product of melting point 240°–255° C. (decomposition). Recrystallization of the crude product from a mixture of 10 ml of chloroform and 50 ml of diethyl ether gave 0.21 g of pure 3'-O-acetyl-2',5'-dideoxy-5-ethyl-5'-(9-fluorenylcarboxamido)uridine of melting point 263°–265° C. (decomposition).

EXAMPLE 26

In a manner analogous to that described in Example 25, there are obtained:

(A) from 2.75 g of 2',5'-dideoxy-5-ethyl-5'-(9-fluorenylcarboxamido)uridine and 1 ml of butyryl chloride there was obtained, after chromatography on silica gel using methylene chloride/methanol (19:1) for the elution, 0.98 g of 3'-O-butyryl-2',5'-dideoxy-5-ethyl-5'-(9-fluorenylcarboxamido)uridine of melting point 208°–210° C. (decomposition).

(B) from 0.45 g of 2',5'-dideoxy-5-ethyl-5'-(9-fluorenylcarboxamido)uridine and 0.22 g of tert.butylacetyl chloride there was obtained, after chromatography on silica gel using methylene chloride for the elution and trituration with petroleum ether (b.p. 40°–60° C.), 0.14 g of 2',5'-dideoxy-5-ethyl-3'-O-(3,3-dimethylbutyryl)-5'-(9-fluorenylcarboxamido)uridine of melting point 100°–110° C. (decomposition).

(C) from 0.45 g of 2',5'-dideoxy-5-ethyl-5'-(9-fluorenylcarboxamido)uridine and 0.3 of palmitoyl chloride there was obtained, after recrystallization from a mixture of 12 ml of ethyl acetate and 48 ml of petroleum ether (b.p. 40°–60° C.), 0.14 g of 2',5'-dideoxy-5-ethyl-5'-(9-fluorenylcarboxamido)-3'-O-(hexadecanoyl-)uridine of melting point 154°–157° C. (decomposition).

EXAMPLE 27

A slurry of 5.5 g of 9-fluorenecarboxylic acid in 100 ml of benzene was stirred at 25° C. and there were then added 3.6 g of oxalyl chloride followed by 0.1 ml of dimethylformamide. The mixture was stirred for 1.5 hours and then evaporated to give the acid chloride in the form of a gum. This gum was cooled to −15° C. and treated with 90 ml of cold (−10° C.) pyridine. 3.3 g of 5'-amino-2',5'-dideoxy-5-ethyluridine were added and the mixture was stirred at a temperature below 0° C. for 2.5 hours to give a pale yellow solution which was left to stand at 4° C. overnight. The solvent was removed by evaporation and the residue was re-evaporated with toluene. The residue was triturated with 70 ml of water to give a gum which, after trituration with 70 ml of ethanol, gave 3.4 g of almost pure product of melting point 240°–245° C. (decomposition). Recrystallization from a mixture of 110 ml of methylene chloride and 110 ml of diethyl ether gave 2.3 g of pure 2',5'-dideoxy-5-ethyl-3'-O-(9-fluorenylcarbonyl)-5'-(9-fluorenylcarboxamido)uridine of melting point 240°–245° C. (decomposition).

EXAMPLE 28

(A) 1.25 of 1M sodium hydroxide solution were added to 0.255 g of 5'-amino-2',5'-dideoxy-5-ethyluridine in 5 ml of water and then 0.2 g of 2-phenylbutyryl chloride was added to the mixture. The resulting mixture was shaken for 10 minutes, whereby a white solid was deposited. This solid was collected by filtration, washed three times with 5 ml of water each time, dried at 50° C. in vacuo over phosphorus pentoxide and recrystallized from ethanol to give 0.28 g of 2',5'-dideoxy-5-ethyl-5'-(2-phenylbutyramido)uridine of melting point 235°–236° C.

(B) In an analogous manner, there were obtained:

(a) from 5'-amino-2',5'-dideoxy-5-ethyluridine and 3-phenylbutyryl chloride:
2',5'dideoxy-5-ethyl-5'-(3-phenylbutyramido)uridine, mp 222°–223° C.;

(b) from 5'-amino-2',5'-dideoxy-5-ethyluridine and diphenylacetyl chloride:
2',5'-dideoxy-5-ethyl-5'-(2,2-diphenylacetamido)uridine, mp 208°–210° C.; and (c) from 5'-amino-2',5'-dideoxy-5-ethyluridine and cyclohexylphenylacetyl chloride:
5'-(2-cyclohexyl-2-phenylacetamido)-2',5'-dideoxy-5-ethyluridine of melting point 130°–132° C.

EXAMPLE 29

A slurry of 0.4 g of triphenylacetic acid in 10 ml of benzene was stirred at 25° C. and treated with 0.2 g of oxalyl chloride and 1 drop of dimethylformamide. Effervesence occurred over a period of about 30 minutes, after which time a solution was obtained. This solution was left to stand at room temperature for 1.5 hours and was then evaporated to give triphenylacetyl chloride in the form of an oil. The acid chloride was cooled to about −10° C. by means of an ice/salt bath and 10 ml of dry pyridine and 0.36 g of 5'-amino-2',5'-dideoxy-5-ethyluridine were added. The mixture was shaken for about 15 minutes, whereby the acid chloride dissolved and the temperature rose to 0° C. The solution was then stirred at 0° C. for 4 hours and then evaporated. The residue was re-evaporated three times with toluene, there being obtained a gum which was triturated with 20 ml of water to give 0.66 g of a solid of melting point 110°–140° C. Recrystallization from 12 ml of ethanol removed residual triphenylacetic acid and the residue was chromatographed on a column of silica gel using methylene chloride/methanol (9:1) for the elution. Recrystallization from a mixture of 5 ml of toluene, 10 ml of cyclohexane and 0.1 ml of ethyl acetate gave 0.25 g of 2',5'-dideoxy-5-ethyl-5'-(triphenylacetamido)uridine of melting point about 110°–120° C. (decomposition).

EXAMPLE 30

In a manner analogous to that described in Example 29, from 0.66 g of 2-phenylisobutyric acid and 0.89 g of 5'-amino-2',5'-dideoxy-5-ethyluridine there was obtained, after chromatography and trituration with diethyl ether, 0.23 g of 2',5'-dideoxy-5-ethyl-5'-(2-methyl-2-phenylpropionamido)uridine of melting point 156°–158° C.

EXAMPLE 31

In a manner analogous to that described in Example 29, but using thionyl chloride to produce the acid chloride, from 0.55 ml of 2(RS)-phenylpropionic acid and 0.89 g of 5'-amino-2',5'-dideoxy-5-ethyluridine there was obtained, after recrystallization from ethanol, 0.59 g of 2',5'-dideoxy-5-ethyl-5'-[2(RS)-phenylpropionamido)]uridine of melting point 237°–239° C.

EXAMPLE 32

(A) A suspension of 2.35 g of 2(RS)-(2,4-dichlorophenoxy)propionic acid in a mixture of 50 ml of benzene, 20 ml of oxalyl chloride and 0.1 ml dimethylformamide was stirred at room temperature for 1.5 hours. The mixture was evaporated to dryness and a solution of the residue in 50 ml of diethyl ether was added to a solution of 2.55 g of 5'-amino-2',5'-dideoxy-5-ethyluridine in 40 ml of 0.25M sodium hydroxide solution. The mixture was shaken vigorously for 10 minutes and then filtered. The solid was washed with 100 ml of water and with 50 ml of diethyl ether and recrystallized from 1 l of ethanol to give 2.31 g of 5'-[2(RS)-(2,4-dichlorophenoxy)propionamido]-2',5'-dideoxy-5-ethyluridine in the form of a white solid of melting point 240°–243° C.

(B) In an analogous manner, there were obtained:
(1) from 2(RS)-(2,6-dichlorophenoxy)propionic acid and 5'-amino-2',5'-dideoxy-5-ethyluridine:
5'-[2(RS)-(2,6-dichlorophenoxy)propionamido]-2',5'-dideoxy-5-ethyluridine, mp 206° C.;
(2) from 2(RS)-(3,5-dichlorophenoxy)propionic acid and 5'-amino-2',5'-dideoxy-5-ethyluridine:
5'-[2(RS)-(3,5-dichlorophenoxy)propionamido]-2',5'-dideoxy-5-ethyluridine, mp 224°–226° C.;
(3) from 2(RS)-(2-chlorophenoxy)propionic acid and 5'-amino-2',5'-dideoxy-5-ethyluridine:
5'-[2(RS)-(2-chlorophenoxy)propionamido]-2',5'-dideoxy-5-ethyluridine, mp 204°–206° C.;
(4) from 2-(2,6-dichlorophenoxy)acetic acid and 5'-amino-2',5'-dideoxy-5-ethyluridine:
5'-[2-(2,6-dichlorophenoxy)acetamido]-2',5'-dideoxy-5-ethyluridine, mp of 193.5°–194° C.;
(5) from 2-(2,4-dichlorophenoxy)acetic acid and 5'-amino-2',5'-dideoxy-5-ethyluridine:
5'-[2-(2,4-dichlorophenoxy)acetamido]-2',5'-dideoxy-5-ethyluridine, mp 191°–193° C.;
(6) from 4-(2,6-dichlorophenoxy)butanoic acid and 5'-amino-2',5'-dideoxy-5-ethyluridine:
5'-[4-(2,6-dichlorophenoxy)butyramido]-2',5'-dideoxy-5-ethyluridine, mp 218°–220° C.;
(7) from 6-(2,6-dichlorophenoxy)hexanoic acid and 5'-amino-2',5'-dideoxy-5-ethyluridine:
5'-[6-(2,6-dichlorophenoxy)hexanamido]-2',5'-dideoxy-5-ethyluridine, mp 219°–221° C.;
(8) from 5-(2,6-dichlorophenoxy)pentanoic acid and 5'-amino-2',5'-dideoxy-5-ethyluridine:
5'-[5-(2,6-dichlorophenoxy)valeramido]-2',5'-dideoxy-5-ethyluridine, mp 215°–217° C.;
(9) from 3-(2,6-dichlorophenoxy)propionic acid and 5'-amino-2',5'-dideoxy-5-ethyluridine:
5'-[3-(2,6-dichlorophenoxy)propionamido]-2',5'-dideoxy-5-ethyluridine, mp 217°–218° C.;
(10) from [2(RS)-(2-chloro-4-nitrophenoxy)]propionic acid and 5'-amino-2',5'-dideoxy-5-ethyluridine:
5'-[2(RS)-(2-chloro-4-nitrophenoxy)propionamido]-2',5'-dideoxy-5-ethyluridine, mp 214°–216° C.;
(11) from [2(RS)-(2-chloro-4-phenylphenoxy)propionic acid and 5'-amino-2',5'-dideoxy-5-ethyluridine:
5'-[2(RS)-(2-chloro-4-phenylphenoxy)propionamido]-2',5'-dideoxy-5-ethyluridine, mp 219°–228° C.;
(12) from 2(R)-(2,4-dichlorophenoxy)propionic acid and 5'-amino-2',5'-dideoxy-5-ethyluridine:
5'-[2(R)-(2,4-dichlorophenoxy)propionamido]-2',5'-dideoxy-5-ethyluridine, mp 230°–231° C.;
(13) from 2(S)-(2,4-dichlorophenoxy)propionic acid and 5'-amino-2',5'-dideoxy-5-ethyluridine:
5'-[2(S)-(2,4-dichlorophenoxy)propionamido]-2',5'-dideoxy-5-ethyluridine, mp 260.5°–261.5° C.;
(14) from (2(RS)-(2,4,5-trichlorophenoxy)propionic acid and 5'-amino-2',5'-dideoxy-5-ethyluridine:
5'-[2(RS)-(2,4,5-trichlorophenoxy)propionamido]-2',5'-dideoxy-5-ethyluridine, mp 255°–257° C.;
(15) from 2(RS)-(2,4-dichlorophenoxy)butyric acid and 5'-amino-2',5'-dideoxy-5-ethyluridine:
5'-[2(RS)-(2,4-dichlorophenoxy)butyramido]-2',5'-dideoxy-5-ethyluridine, mp 223°–227° C.;
(16) from 2(RS)-(4-chloro-2-nitrophenoxy)propionic acid and 5'-amino-2',5'-dideoxy-5-ethyluridine:
5'-[2(RS)-(4-chloro-2-nitrophenoxy)propionamido]-2',5'-dideoxy-5-ethyluridine, mp 199°–201° C.;
(17) from 2(RS)-(4-acetamido-2-chlorophenoxy)propionic acid and 5'-amino-2',5'-dideoxy-5-ethyluridine:
5'-[2(RS)-(4-acetamido-2-chlorophenoxy)propionamido]-2',5'-dideoxy-5-ethyluridine, mp 234°–236° C.;
(18) from 2(RS)-(2,4-dichlorophenoxy)-2-phenylacetic acid and 5'-amino-2',5'-dideoxy-5-ethyluridine:
5'-[2(RS)-(2,4-dichlorophenoxy)-2-phenylacetamido]-2',5'-dideoxy-5-ethyluridine, mp 120°–125° C.;
(19) from 2(RS)-(2,4-dichloro-5-methoxyphenoxy)propionic acid and 5'-amino-2',5'-dideoxy-5-ethyluridine:
5'-[2(RS)-(2,4-dichloro-5-methoxyphenoxy)propionamido]-2',5'-dideoxy-5-ethyluridine, mp 191°–194° C.;
(20) from 2(RS)-(2-chloro-4-methoxyphenoxy)propionic acid and 5'-amino-2',5'-dideoxy-5-ethyluridine:
5'-[2(RS)-(2-chloro-4-methoxyphenoxy)propionamido]-2',5'-dideoxy-5-ethyluridine, mp 215°–221° C.;
(21) from 2(RS)-(2-methylbiphenylyloxy)propionic acid and 5'-amino-2',5'-dideoxy-5-ethyluridine:
2',5'-dideoxy-5-ethyl-5'-[2(RS)-(2-methylbiphenylyloxy)propionamido]uridine, mp 216°–217° C.;
(22) from 2(RS)-(2,4-dichlorophenoxy)propionic acid and 5'-amino-5'-deoxythymidine:
5'-[2(RS)-(2,4-dichlorophenoxy)propionamido]-5'-deoxythymidine, mp 208°–210° C.;
(23) from 2-(2,4-dichlorophenoxy)-2-methylpropionic acid and 5'-amino-2',5'-dideoxy-5-ethyluridine:
5'-[2-(2,4-dichlorophenoxy)-2-methylpropionamido]-2',5'-dideoxy-5-ethyluridine, mp 188°–190° C.;
(24) from 2(RS)-phenoxypropionic acid and 5'-amino-2',5'-dideoxy-5-ethyluridine:
2',5'-dideoxy-5'-[2(RS)-phenoxypropionamido]uridine, mp 214°–216° C.;
(25) from 2(RS)-(2-fluorophenoxy)propionic acid and 5'-amino-2',5'-dideoxy-5-ethyluridine:
2',5'-dideoxy-5-ethyl-5'-[2(RS)-(2-fluorophenoxy)propionamido]uridine, mp 205°–207° C.;
(26) from 2(RS)-(2-trifluoromethylphenoxy)propionic acid and 5'-amino-2',5'-dideoxy-5-ethyluridine:
2',5'-dideoxy-5-ethyl-5'-[2(RS)-(2-trifluoromethylphenoxy)propionamido]uridine, mp 221°–225° C.; and
(27) from 2(RS)-(2-phenylphenoxy)propionic acid and 5'-amino-2',5'-dideoxy-5-ethyluridine:
2',5'-dideoxy-5-ethyl-5'-[2(RS)-(2-phenylphenoxy)propionamido]uridine, mp 206°–207° C.

The 4-(2,6-dichlorophenoxy)butanoic acid referred to earlier was prepared as follows:

Small pieces of sodium (353 mg) were added to a stirred solution of 2.5 g of 2,6-dichlorophenol in 10 ml of ethanol and the mixture was stirred at room temperature until the evolution of gas had ceased. 2.715 g of methyl 4-bromobutyrate were added and the mixture was stirred and heated under reflux for 4 hours. After cooling the mixture was filtered and the filtrate was evaporated to dryness. The residue was dissolved in 50 ml of dichloromethane and the solution was washed with 10% sodium carbonate solution, dried over anhydrous sodium sulfate and evaporated to give 3.62 g of a colorless oil.

The above oil was dissolved in 20 ml of ethanol and the solution was treated with a solution of 0.5 g of potassium hydroxide in 10 ml of water. The mixture was stirred and heated under reflux for 3 hours and then evaporated to dryness. The residue was taken up in 50 ml of saturated sodium hydrogen carbonate solution and the resulting solution was washed twice with 50 ml of dichloromethane each time, acidified with 2M hydrochloric acid and extracted with 50 ml of dichloromethane. The dichloromethane extract was dried over anhydrous sodium sulfate and evaporated to give 1.3 g of 4-(2,6-dichlorophenoxy)butanoic acid in the form of a white crystalline solid of melting point 68°–67° C.

In an analogous manner, from 2,6-dichlorophenol and methyl 6-bromohexanoate there was obtained 6-(2,6-dichlorophenoxy)hexanoic acid; and from 2,6-dichlorophenol and methyl 5-bromopentanoate there was obtained 5-(2,6-dichlorophenoxy)pentanoic acid.

EXAMPLE 33

In a manner analogous to that described in Example 32, from 2(RS)-(2,4-dichlorophenoxy)propionic acid and 1-(5-amino-2,5-dideoxy-2-fluoro-β-D-arabinofuranosyl)-5-ethyluracil there was obtained 1-[5-[2-(RS)-(2,4-dichlorophenoxy)propionamido]-2,5-dideoxy-2-fluoro-β-D-arabinofuranosyl]-5-ethyluracil of melting point 194°–214° C.

The 1-(5-amino-2,5-dideoxy-2-fluoro-β-D-arabinofuranosyl)-5-ethyluracil used above as the starting material was prepared as follows:

A mixture of 0.4 g of 1-(2-deoxy-2-fluoro-β-D-arabinofuranosyl)-5-ethyluracil, 0.44 g of triphenylphosphine, 0.48 g of sodium azide and 6 ml of dry dimethylformamide was stirred at room temperature under nitrogen while 0.48 g of carbon tetrabromide was added portionwise. The mixture was stirred at room temperature under nitrogen for 20 hours. 3 ml of methanol were added, the mixture was stirred for 0.5 hour and then evaporated. The residue was stirred for 0.5 hour with 8 ml of 0.5M sodium hydroxide solution. The resulting suspension was filtered and the insoluble triphenylphosphine oxide was washed with water. The filtrate was acidified to pH 5 by the addition of hydrochloric acid and then extracted three times with 20 ml of ethyl acetate. The extracts were dried over magnesium sulfate, filtered and evaporated. The residual solid was washed on to a filter with 10 ml of diethyl ether/petroleum ether (1:1) and then dried in vacuo to give 0.4 g of 1-(5-azido-2,5-dideoxy-2-fluoro-β-D-arabinofuranosyl)-5-ethyluracil as a white solid of melting point 185°–188° C.

A solution of 0.4 g of 1-(5-azido-2,5-dideoxy-2-fluoro-β-D-arabinofuranosyl)-5-ethyluracil in 20 ml of ethanol was hydrogenated at room temperature and under atmospheric pressure in the presence of 0.1 g of 10% palladium-on-carbon catalyst for 24 hours. The catalyst was removed by filtration and the filtrate was evaporated. The residue was triturated with diethyl ether and the solid was removed by filtration, washed with ethyl acetate and dried in vacuo to give 0.3 g of 1-(5-amino-2,5-dideoxy-2-fluoro-β-D-arabinofuranosyl)-5-ethyluracil as a white solid.

EXAMPLE 34

In a manner analogous to that described in Example 32, from 2(RS)-(2,4-dichlorophenoxy)propionic acid and 1-(5-amino-2,5-dideoxy-2-fluoro-β-D-arabinofuranosyl)thymine there was obtained 1-[5-[2(RS)-(2,4-dichlorophenoxy)propionamido]-2,5-dideoxy-2-fluoro-β-D-arabinofuranosyl]thymidine of melting point 147°–155° C.

The 1-(5-amino-2,5-dideoxy-2-fluoro-β-D-arabinofuranosyl)thymine used as the starting material was prepared from 1-(2-deoxy-2-fluoro-β-D-arabinofuranosyl)thymine in a manner analogous to that described in Example 33 for the preparation of 1-(5-amino-2,5-dideoxy-2-fluoro-β-D-arabinofuranosyl)-5-ethyluracil.

EXAMPLE 35

A suspension of 3.0 g of 2(RS)-(2,4-dichlorophenylthio)propionic acid in a mixture of 50 ml of toluene, 5 ml of oxalyl chloride and 0.1 ml of dimethylformamide was stirred at room temperature for 2.5 hours. The mixture was evaporated to dryness and a solution of the residue in 20 ml of diethyl ether was added to a solution of 3.05 g of 5'-amino-2',5'-dideoxy-5-ethyluridine in 32 ml of 0.375M sodium hydroxide solution. The mixture was shaken vigorously for 5 minutes and then filtered. The solid was washed with water and recrystallized from 600 ml of ethanol to give 3.0 g of 5'-[2(RS)-(2,4-dichlorophenylthio)propionamido]-2',5'-dideoxy-5-ethyluridine in the form of a pale yellow solid of melting pont 218°–220° C.

The 2(RS)-(2,4-dichlorophenythio)propionic acid used as the starting material was prepared as follows:

A mixture of 11.78 g of 2,4-dichlorothiophenol and 12.0 g of potassium hydroxide in 50 ml of acetone was stirred and heated to reflux. 11.77 g of ethyl 2-bromopropionate were added gradually and the mixture was heated under reflux for 22 hours. After cooling to room temperature, the mixture was filtered and the filtrate was evaporated to dryness. The residue was taken up in 400 ml of diethyl ether and the solution was washed with 400 ml of water and 400 ml of 10% sodium carbonate solution, dried over anhydrous sodium sulfate and evaporated to dryness. A solution of the residue in a mixture of 30 ml of ethanol and 17 ml of 10% potassium hydroxide solution was heated under reflux for 21 hours. The solution was evaporated to dryness and the residue was dissolved in 50 ml of water. The resulting solution was washed twice with 50 ml of diethyl ether each time and then acidified with concentrated hydrochloric acid and extracted twice with 150 ml of ethyl acetate each time. The combined organic extracts were washed twice with 200 ml of water each time, dried over anhydrous sodium sulfate and evaporated to dryness. The residue was recrystallized from diethyl ether to give 4.08 g of 2(RS)-(2,4-dichlorophenyl-thio)propionic acid in the form of a yellow solid of melting point 95°–98° C.

EXAMPLE 36

A suspension of 250 mg of 5'-[2(RS)-(2,4-dichlorophenylthio)propionamido]-2',5'-dideoxy-5-ethyluridine in 10 ml of acetic acid was cooled to 0° C. and 60 mg of 30% hydrogen peroxide were added. The mixture was stirred at 0° C. for 0.5 hour and then at room temperature overnight. An additional 60 mg of 30% hydrogen peroxide were added and the mixture was stirred for 24 hours. An additional 30 mg of 30% hydrogen peroxide were added and the mixture was stirred for an additional 4 hours and then evaporated to dryness. The residue was triturated with methanol and the resulting solid was removed by filtration and recrystallized from methanol to give 90 mg of 5'-[2(RS)-(2,4-dichlorophenylsulphinyl)propionamido]-2',5'-dideoxy-5-ethyluridine in the form of a white solid of melting point 208°–209° C.

EXAMPLE 37

A suspension of 250 mg of 5'-[2(RS)-(2,4-dichlorophenylthio)propionamido]-2',5'-dideoxy-5-ethyluridine in 10 ml of acetic acid was cooled to 0° C. and 800 mg of 30% hydrogen peroxide were added. The mixture was stirred at 0° C. for 0.5 hour and then at room temperature overnight. The mixture was evaporated to dryness and the residue was recrystallized from methanol to give 140 mg of 5'-[2(RS)-(2,4-dichlorophenylsulfonyl)propionamido]-2',5'-dideoxy-5-ethyluridine in the form of a white solid of melting point 183°–184° C.

EXAMPLE 38

(A) A suspension of 51 mg of 2,6-dichlorophenylacetic acid in a mixture of 10 ml of toluene, 100 mg of oxalyl chloride and 1 drop of dimethylformamide was stirred at room temperature for 0.5 hour. The mixture was evaporated to dryness and a solution of the residue in 2 ml of diethyl ether was added to a solution of 70 mg of 5'-(2-aminoethyl)-2',5'-dideoxy-5-ethyluridine in 5 ml of 0.1M sodium hydroxide solution. The mixture was shaken vigorously for 5 minutes and then filtered. The solid was washed in succession with water, ethanol and diethyl ether and then dried over anhydrous sodium sulfate to give 90 mg of 5'-[2-(2,6-dichlorophenylacetamido)ethyl]-2',5'-dideoxy-5-ethyluridine in the form of a white solid of melting point 227°–229° C.

(B) In an analogous manner, there were obtained:
(a) from 5'-[2-(aminoethyl)]-2',5'-dideoxy-5-ethyluridine and 2(RS)-(2,4,5-trichlorophenoxy)propionic acid:
5'-[2-[2(RS)-(2,4,5-trichlorophenoxy)propionamido]ethyl]-2',5'-dideoxy-5-ethyluridine, mp 184°–185° C.; and
(b) from 5'-[2-(aminoethyl)]-2',5'-dideoxy-5-ethyluridine and 2(RS)-(2,4-dichlorophenoxy)propionic acid:
5'-[2-[2(RS)-(2,4-dichlorophenoxy)propionamido]ethyl]-2',5'-dideoxy-5-ethyluridine of melting point 170°–172° C.

The 5'-(2-aminoethyl)-2',5'-dideoxy-5-ethyluridine used above as the starting material was prepared as follows:

1.9 g of dichloroacetic acid were added to a mixture of 8.95 g of 3'-O-acetyl-2',5'-dideoxy-5-ethyluridine and 18.6 g of dicyclohexylcarbodiimide in 75 ml of dimethyl sulfoxide. The mixture was stirred at room temperature for 24 hours. 1.2 ml of pyridine and 10.5 g of carbethoxymethylenetriphenylphosphorane were added and the mixture was stirred at room temperature for an additional 24 hours. The solvent was removed in vacuo and the residue was dissolved in 300 ml of ethyl acetate. The solution was washed with 300 ml of water, dried over anhydrous sodium sulfate and evaporated to give a yellow oil. This oil was subjected to flash chromatography on a column of silica gel using 5% methanol/dichloromethane for the elution. The product was recrystallized from ethanol to give 7.3 g of trans-3'-O-acetyl-2',5'-dideoxy-5'-(ethoxycarbonylmethylene)-5-ethyluridine in the form of a white solid of melting point 132°–133° C.

A solution of 7.3 g of trans-3'-O-acetyl-2',5'-dideoxy-5'-(ethoxycarbonylmethylene)-5-ethyluridine in 150 ml of ethanol was hydrogenated over 0.5 g of 10% palladium-on-carbon catalyst for 6 hours. The catalyst was removed by filtration and the filtrate was evaporated to dryness. The residue was recrystallized from ethanol to give 5.8 g of 3'-O-acetyl-2',5'-dideoxy-5'-(ethoxycarbonylmethyl)-5-ethyluridine in the form of a white solid of melting point 137°–138° C.

0.4 g of lithium borohydride was added to a solution of 5.6 g of 3'-O-acetyl-2',5'-dideoxy-5'-(ethoxycarbonylmethyl)-5-ethyluridine in 100 ml of tetrahydrofuran and the mixture was stirred at room temperature for 4 hours. An additional 0.2 g of lithium borohydride was added and the mixture was stirred at room temperature overnight and then heated under reflux for 1 hour. The solvent was removed by evaporation in vacuo and the residue was dissolved in methanol. After standing at room temperature for a few minutes, the solvent was removed by evaporation and the residue was taken up in 40 ml of pyridine. 5 g of acetic anhydride were added and the mixture was stirred at room temperature overnight. Pyridine was removed by evaporation and the residue was partitioned between water and ethyl acetate. The aqueous solution was evaporated to dryness and the residue was subjected to flash chromatography on a column of silica gel using 10% methanol/dichloromethane for the elution to give 1.3 g of 5'-(2-acetoxyethyl)-3'-O-acetyl-2',5'-dideoxy-5-ethyluridine in the form of a colorless oil which crystallized upon standing.

0.10 g of 5'-(2-acetoxyethyl)-3'-O-acetyl-2',5'-dideoxy-5-ethyluridine was treated with 5 ml of a dilute solution of sodium methoxide in methanol. After standing at room temperature for 2 hours the solution was neutralized by the addition of a cross-linked polystyrene-divinylbenzene cation exchange resin containing sulfonic acid groups (H+ form) and then filtered. The filtrate was evaporated to dryness to give 0.045 g of 2',5'-dideoxy-5-ethyl-5'-(2-hydroxyethyl)uridine in the form of a white solid of melting point 113°–115° C.

A mixture of 1.25 g of 2',5'-dideoxy-5-ethyl-5'-(2-hydroxyethyl)uridine, 1.18 g of triphenylphosphine, 1.49 g of sodium azide and 1.55 g of carbon tetrabromide in 30 ml of dimethylformamide was stirred at room temperature overnight. The mixture was evaporated to dryness and the residue was partitioned between ethyl acetate and water. The ethyl acetate solution was evaporated to dryness and the residue was subjected to flash chromatography on a column of silica gel using 1% methanol/dichloromethane for the elution to give 0.28 g of 5'-(2-azidoethyl)-2',5'-dideoxy-5-ethyluridine in the form of a colorless oil which crystallized upon standing.

A solution of 0.28 of 5'-(2-azidoethyl)-2',5'-dideoxy-5-ethyluridine in 50 ml of ethanol was hydrogenated over 50 mg of 10% palladium-on-carbon catalyst for 2 hours. The catalyst was removed by filtration and the filtrate was evaporated to dryness to give 0.23 g of 5'-(2-aminoethyl)-2',5'-dideoxy-5-ethyluridine in the form of a colorless oil which crystallized upon standing.

EXAMPLE 39

0.175 g of 2(RS)-(2,6-dichlorobenzyl)propionic acid was dissolved in 5 ml of dry benzene containing 1 drop of dimethylformamide. 96 mg of oxalyl chloride were then added. After 1 hour the solvent was removed by evaporation. The residue was treated with a solution of 5'-amino-2',5'-dideoxy-5-ethyluridine in 5 ml of an aqueous solution containing 3 ml of 2M sodium hydroxide solution. The mixture was shaken for 15 minutes. The resulting precipitate was removed by filtration, dried over anhydrous sodium sulfate and recrystallized from a mixture of ethanol and diethyl ether to give 0.11 g of 5'-[2(RS)-(2,6-dichlorobenzyl)propionamido]-2',5'-dideoxy-5-ethyluridine of melting point 194°–197° C.

The 2(RS)-(2,6-dichlorobenzyl)propionic acid used as the starting material was prepared as follows:

2.4 g of triethyl 2-phosphinopropionate and 1.75 g of 2,6-dichlorobenzaldehyde were dissolved in 15 ml of dry dimethylformamide. 0.29 g of a 80% dispersion of sodium hydride in mineral oil was added portionwise and the mixture was stirred for 2 hours. 100 ml of water were added and the mixture was extracted three times with 40 ml of methylene chloride each time. The combined methylene chloride extracts were back-washed twice with 50 ml of sodium chloride solution each time and the solvent was removed by evaporation to give 2.4 g of ethyl 2,6-dichloro-2-methylcinnamate in the form of an oil.

0.26 g of ethyl 2,6-dichloro-2-methylcinnamate were dissolved in 10 ml of methanol and the solution was treated with 0.96 g of magnesium turnings and stirred. The mixture was cooled to −5° C. to 0° C. in an ice-salt bath and maintained at this temperature for 1 hour. The mixture was then held at room temperature for 4 hours. 25 ml of 6M hydrochloric acid were added dropwise during 20 minutes to give a clear solution. The solution was extracted three times with 15 ml of diethyl ether each time and the combined extracts were dried over anhydrous sodium sulfate and evaporated to give 0.21 g of a colorless oil which, according to nmr spectroscopy, was a 2:1 mixture of methyl and ethyl 2(RS)-(2,6-dichlorobenzyl)propionate.

0.20 g of the above mixture was dissolved in a mixture of 5 ml of 10% potassium hydroxide solution and 5 ml of ethanol. The solution was heated under reflux for 'hours. The ethanol was removed by evaporation and the residue was cooled and acidified with concentrated hydrochloric acid. Extraction with three 10 ml portions of ethyl acetate, washing with sodium chloride solution, drying over anhydrous sodium sulfate and evaporation of the solvent gave 0.18 g of 2(RS)-(2,6-dichlorobenzyl)propionic acid as an oil.

EXAMPLE 40

In a manner analogous to that described in Example 39, there were obtained:

(A) from 0.21 g of 2(RS)-(2,4-dichlorobenzyl)propionic acid and 0.20 g of 5'-amino-2',5'-dideoxy-5-ethyluridine:

0.35 g of 5'-[2(RS)-(2,4-dichlorobenzyl)propionamido]-2',5'-dideoxy-5-ethyluridine, mp 243°–245° C.

(B) from 0.20 g of 5-chloro-2,3-dihydro-2(RS)-benzofurancarboxylic acid and 0.26 g of 5'-amino-2',5'-dideoxy-5-ethyluridine:

0.10 g of 5'-[5-chloro-2,3-dihydro-2(RS)-benzofuranylcarboxamido]-2',5'-dideoxy-5-ethyluridine, mp 204°–206° C.

(C) from 0.10 g of 6-chlorochroman-2-carboxylic acid and 0.12 g of 5'-amino-2',5'-dideoxy-5-ethyluridine:

20 mg of 5-(6-chloro-2H-1-benzopyran-2-ylcarboxamido)-5'-dideoxy-5-ethyluridine, mp 171°–176° C.

EXAMPLE 41

In a manner analogous to that described in Example 15, from 0.335 g of 2-(4-benzyloxy-2,6-dimethylphenyl)acetic acid and 0.28 g of 5'-amino-2',5'-dideoxy-5-ethyluridine there was obtained, after recrystallization from a mixture of 2-methoxyethanol and water, 0.33 g of 5'-[2-(4-benzyloxy-2,6-dimethylphenyl)acetamido]-2',5'-dideoxy-5-ethyluridine of melting point 259°–260° C.

The 2-(4-benzyloxy-2,6-dimethylphenyl)acetic acid used as the starting material was prepared as follows:

0.36 g of 2-(4-hydroxy-2,6-dimethylphenyl)acetic acid was treated with 184 mg of a 60% dispersion of sodium hydride in mineral oil and 0.72 g of benzyl bromide in 10 ml of dry dimethylformamide. The solvent was removed by evaporation and the residue was partitioned between water and methylene chloride. The organic layer was evaporated to give 0.63 g of crude product of melting point 54°–57° C. Recrystallization from aqueous methanol gave 0.58 g of pure benzyl 2-(4-benzyloxy-2,6-dimethylphenyl)acetate of melting point 62°–64° C.

0.35 g of benzyl 2-(4-benzyloxy-2,6-dimethylphenyl)acetate was shaken overnight with a mixture of 7 ml of methanol, 0.7 ml of water and 0.28 g of solid sodium hydroxide. The resulting solution was evaporated and the residue was partitioned between 50 ml of methylene chloride and 25 ml of 2M hydrochloric acid. The organic layer was dried over anhydrous sodium sulfate and evaporated. The solid residue was recrystallized from a mixture of 3 ml of methanol and 3 ml of water to give 0.21 g of 2-(4-benzyloxy-2,6-dimethylphenyl)acetic acid of melting point 149°–150° C.

EXAMPLE 42

0.25 g of 5'-[2-(4-benzyloxy-2,6-dimethylphenyl)acetamido]-2',5'-dideoxy-5-ethyluridine was stirred as a slurry in 5 ml of dry pyridine with 0.4 ml of acetic anhydride for 72 hours. The resulting solution was evaporated in vacuo and the residue was re-evaporated three times with toluene. After trituration with diethyl ether and filtration there was obtained 0.22 g of crude product of melting point 188°–191° C. Recrystallization from a mixture of 4 ml of methylene chloride and 4 ml of petroleum ether gave 0.20 g of pure 3'-O-acetyl-5'-[2-(4-benzyloxy-2,6-dimethylphenyl)acetamido]-2',5'-dideoxy-5-ethyluridine of melting point 194°–196° C. (dec).

EXAMPLE 43

0.165 g of 3'-O-acetyl-5'-[2-(4-benzyloxy-2,6-dimethylphenyl)acetamido]-2',5'-dideoxy-5-ethyluridine was dissolved in 25 ml of methanol. A slurry of 0.1 g of 5% palladium-on-charcoal catalyst in ethanol was added. The mixture was hydrogenated at room temperature and under atmospheric pressure for 2 hours. The catalyst was removed by filtration and the filtrate was evaporated to give 0.125 g of solid of melting point 234°–237° C. Recrystallization from a mixture of 10 ml of acetone and 20 ml of petroleum ether gave 80 mg of 3'-O-acetyl-2',5'-dideoxy-5-ethyl-5'-[2-(4-hydroxy-2,6-dimethylphenyl)acetamido]uridine of melting point 240°–241° C. (dec).

EXAMPLE 44

24 mg of 5'-[2-(4-benzyloxy-2,6-dimethylphenyl)acetamido]-2',5'-dideoxy-5-ethyluridine were dissolved in 50 ml of methanol and the solution was hydrogenated over 15 mg of 5% palladium-on-charcoal catalyst at room temperature and under atmospheric pressure for 72 hours. The catalyst was removed by filtration and the filtrate was evaporated to give 15 mg of 2',5'-dideoxy-5-ethyl-5'-[2-(4-hydroxy-2,6-dimethylphenyl)acetamido]uridine of melting point 221°–225° C. (decomposition).

EXAMPLE 45

95 mg of 3'-O-acetyl-2',5'-dideoxy-5-ethyl-5'-[2-(4-hydroxy-2,6-dimethylphenyl)acetamido]uridine were dissolved in 5 ml of dry dimethylformamide while stirring magnetically at room temperature. 69 mg of a 60% dispersion of sodium hydride in mineral oil were added and the mixture was stirred for 1 hour. 68 mg of freshly prepared dibenzylphosphoryl chloride in 2 ml of dry benzene were added and the mixture was stirred at room temperature for 18 hours. The mixture was poured into 30 ml of saturated aqueous sodium bicarbonate solution and the product was extracted with ethyl acetate. The extract was evaporated to give an oil which was purified by flash chromatography on silica gel using 5% methanol/dichloromethane for the elution. The solvent was removed by evaporation to give 65 mg of product which, after trituration with petroleum ether (boiling point 60°–80° C.), gave 3'-O-acetyl-2',5'-dideoxy-5-ethyl-5'-[2-(2,6-dimethyl-4-(dibenzyloxyphosphinyloxy)phenyl]acetamido]uridine in the form of a white crystalline solid.

The above solid was taken up in 10 ml of a saturated solution of ammonia in methanol at room temperature and left to stand overnight. The solvent was removed by evaporation to give 2',5'-dideoxy-5-ethyl-5'-[2-[2,6-dimethyl-4-(dibenzyloxyphosphinyloxy)phenyl]acetamido]uridine in the form of a solid.

60 mg of the above solid were suspended in 10 ml of ethanol. 10 mg of 10% palladium-on-charcoal catalyst were added and the mixture was hydrogenated at room temperature and under atmospheric pressure for 4 hours. The catalyst was removed by filtration and washed with several portions of warm ethanol. The combined filtrates were evaporated to give 40 mg of 2',5'-dideoxy-5-ethyl-5'-[2-(2,6-dimethyl-4-phosphatophenyl)acetamido]uridine of melting point 214°–216° C.

EXAMPLE 46

(A) In a manner analogous to that described in Example 16, from 0.22 g of (RS)-(2,4-dichlorophenoxy)propionic acid and 0.27 g of 5'-amino-5-(2-chloroethyl)-2',5'-dideoxyuridine hydrochloride there was obtained, after recrystallization from a mixture of 2-methoxyethanol and water, 0.13 g of 5-(2-chloroethyl)-2',5'-dideoxy-5'-[2-(2,4-dichlorophenoxy)propionamido]uridine of melting point 214°–216° C., (B) from 55 mg of benzoyl chloride and 115 mg of 5'-amino-5-(2-chloroethyl)-2',5'-dideoxyuridine hydrochloride there were obtained, after recrystallization from a mixture of 2-methoxyethanol and water, 70 mg of 5'-benzamido-5-(2-chloroethyl)-2',5'-dideoxyuridine of melting point 249°–250° C. (decomposition), (C) from 104 mg of 2-(2,4,5-trichlorophenoxy)propionic acid and 115 mg of 5'-amino-5-(2-chloroethyl)-2',5'-dideoxyuridine hydrochloride there were obtained, after recrystallization from a mixture of 2-methoxyethanol and water, 95 mg of 5-(2-chloroethyl)-5'-[2-(2,4,5-trichlorophenoxy)propionamido]-2',5'-dideoxyuridine of melting point 223°–225° C., (D) from 136 mg of 2,6-dichlorophenylacetic acid and 0.16 g of 5'-amino-2',5'-dideoxy-5-n-propyluridine there was obtained, after recrystallization from a mixture of 2-methoxyethanol and water, 0.21 g of 5'-[2-(2,6-dichlorophenyl)acetamido]-2',5'-dideoxy-5-propyluridine of melting point 297°–298° C. (decomposition).

The 5'-amino-2',5'-dideoxy-5-n-propyluridine used as the starting material was prepared as follows:

0.57 g of 2'-deoxy-5-n-propyluridine, 0.6 g of triphenylphosphine and 0.69 g of sodium azide were stirred in 20 ml of dry dimethylformamide. 0.77 g of carbon tetrabromide was added over a period of 5 minutes. The mixture was stirred at room temperature for 72 hours, 20 ml of methanol were added and the mixture was stirred for a further 0.5 hour. The mixture was evaporated and the residue was stirred with a mixture of 25 ml of dichloromethane/methanol (8:2). An insoluble solid was removed by filtration and the filtrate was chromatographed on 200 g of silica gel in the same solvent mixture to give 0.41 g of 5'-azido-2',5'-dideoxy-5-n-propyluridine of melting point 177°–179° C. (decomposition).

0.38 g of 5'-azido-2',5'-dideoxy-5-n-propyluridine was dissolved in 100 ml of ethanol and the solution was hydrogenated in the presence of 0.1 g of 10% palladium-on-charcoal catalyst for 2 hours at room temperature and under atmospheric pressure. The catalyst was removed by filtration and the filtrate was evaporated to give 5'-amino-2',5'-dideoxy-5-n-propyluridine in the form of a solid which was used without further purification.

EXAMPLE 47

In a manner analogous to that described in Example 46D, from 155 mg of 2(RS)-(2,4-dichlorophenoxy)propionic acid and 0.16 g of 5'-amino-2',5'-dideoxy-5-n-propyluridine there was obtained 0.20 g of 5-[2(RS)-(2,4-dichlorophenoxy)propionamido]-2',5'-dideoxy-5-propyluridine of melting point 232°–243° C. (decomposition).

EXAMPLE 48

In a manner analogous to that described in Example 16, from 0.23 g of 2,6-dichlorophenylacetic acid and 0.31 g of 5-acetyl-5'-amino-2',5'-dideoxyuridine hydrochloride there were obtained, after recrystallization from a mixture of ethanol and petroleum ether, 60 mg of 5-acetyl-5'-[2-(2,6-dichlorophenyl)acetamido]-2',5'-dideoxyuridine of melting point 210°–212° C. (dec.).

The 5-acetyl-5'-amino-2',5'-dideoxyuridine hydrochloride used as the starting material was prepared as follows:

1.26 g of 5-acetyl-2'-deoxyuridine, 1.35 g of triphenylphosphine, 1.52 g of sodium azide and 1.7 g of carbon tetrabromide in 40 ml of dimethylformamide were reacted as described in Example 54 and the product was purified by chromatography on 400 g of silica gel in dichloromethane/methanol (9:1) to give 0.80 g of 5- acetyl-5'-azido-2',5'-dideoxyuridine of melting point 159°–162° C. (decomposition).

0.80 g of 5-acetyl-5'-azido-2',5'-dideoxyuridine was dissolved in 100 ml of methanol and 10 ml of 0.27M hydrogen chloride in methanol were added. 0.1 g of 5% palladium-on-charcoal catalyst was added as a slurry in ethanol and the mixture was hydrogenated for 3 hours at room temperature and under atmospheric pressure. The catalyst was removed by filtration and the filtrate was evaporated to give 0.91 g of hygro-scopic 5-acetyl-5'-amino-2',5'-dideoxyuridine hydrochloride of melting point 73°–85° C. (decomposition).

The following Example illustrates a pharmaceutical preparation containing a compound of formula I:

Tablets may contain the following ingredients:

| Ingredient | Per tablet |
|---|---|
| Compound of formula I | 100 mg |
| Lactose | 70 mg |
| Maize starch | 70 mg |
| Polyvinylpyrrolidone | 5 mg |
| Magnesium stearate | 5 mg |
| Tablet weight | 250 mg |

We claim:

1. A compound of the formula

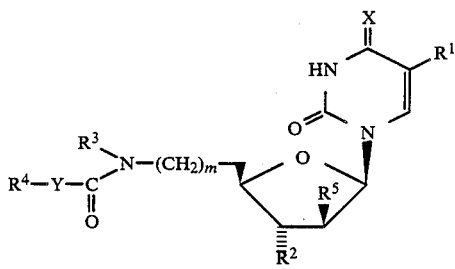

wherein
$R^1$ is halogen, $C_{1-4}$-alkyl, halo-($C_{1-4}$-alkyl) or $C_{2-4}$-alkanoyl,
$R^2$ is hydrogen, hydroxy, $C_{1-4}$-alkoxy-$C_{1-4}$-alkylthio phenyl-($C_{1-4}$-alkoxy) or $C_{2-4}$-alkanoyloxy,
$R^3$ is hydrogen or $C_{1-4}$-alkyl,
$R^4$ is a carbocyclic group selected from the group consisting of 2-biphenylyl, 4-biphenylyl, 3-chloro-4-biphenylyl, 1-naphthyl, 2-naphthyl, cyclopentyl, cyclohexyl, adamantyl, indanyl, fluorenyl and phenyl which may be substituted by one or more substituents selected from the group consisting of halogen, hydroxy, $C_{1-4}$-alkyl, $C_{1-4}$-alkoxy, trifluoromethyl, phenyl, $C_{1-4}$-alkylphenyl, halophenyl, nitro, amino, $C_{2-4}$-alkanoylamino, benzyloxy and O-phosphate, or is a heterocyclic group selected from the group consisting of 2-furyl, 2-thienyl, 3-thienyl, 2-pyridyl, 3-pyridyl, 2-benzofuranyl, 2,3-dihydro-2-benzofuranyl, 2-benzothienyl, 2-quinolyl and 2-benzopyranyl
$R^5$ is hydrogen or fluorine,
m stands for zero, 1 or 2,
X is O and Y is a direct bond, —CH=CH—, —C≡C— or a group of the formula of $$-(Z)_n-A-$$ (a)

in which A is a $C_{1-8}$-alkylene group which may be substituted by one or two phenyl groups, Z is O, S, SO or $SO_2$ and n stands for zero or 1, with the proviso that $R^1$ is different from iodine, when $R^2$ is hydroxy or benzoyloxy, $R^3$ is hydrogen, $R^4$ is unsubstituted phenyl, $R^5$ is hydrogen, m stands for zero, X is O, and Y is a direct bond, or a tautomer thereof.

2. A compound according to claim 1, wherein $R^1$ is fluorine, chlorine, bromine, $C_{1-4}$-alkyl or halo-($C_{1-4}$-alkyl), $R^4$ is a carbocyclic group as defined in claim 1, $R^5$ is hydrogen and m is zero.

3. A compound according to claim 2, wherein $R^1$ is $C_{1-4}$-alkyl.

4. A compound according to claim 3, wherein $R^2$ is hydroxy.

5. A compound according to claim 4, wherein $R^3$ is hydrogen.

6. A compound according to claim 5, wherein $R^4$ is phenyl which may be substitued by one or more substituents selected from the group consisting of halogen, $C_{1-4}$-alkyl, $C_{1-4}$-alkoxy, trifluoromethyl, phenyl and nitro.

7. A compound according to claim 6, wherein m is zero.

8. A compound according to claim 7, wherein X is O.

9. A compound according to claim 8, wherein Y is a group of formula (a).

10. A compound according to claim 7, wherein $R^1$ is ethyl, $R^2$ is hydroxy, $R^3$ is hydrogen, $R^4$ is 2-bromophenyl, 2,6-dichlorophenyl or 4-biphenylyl, m is zero, X is O and Y is a group of formula (a) as defined in claim 1 in which A is —$CH_2$ or —$CH(CH_3)$— and n is zero.

11. A compound according to claim 7, wherein $R^1$ is ethyl or propyl, $R^2$ is hydroxy, $R^3$ is hydrogen, $R^4$ is 2-biphenylyl, 2,4-dichlorophenyl, 2,4,5-trichlorophenyl, 4-chloro-2-nitrophenyl or 2,4-dichloro-5-methoxyphenyl, m is zero, X is O and Y is a group of formula (a) as defined in claim 1 in which A is —$CH(CH_3)$— or —CH(phenyl)—, Z is O and n is 1.

12. A compound according to claim 1, selected from the group consisting of
5'-[2-(2-bromophenyl)acetamido]-2',5'-dideoxy-5-ethyluridine,
5'-[2-(2,6-bichlorophenyl)acetamido]-2',5'-dideoxy-5-ethyluridine,
5'-[2(RS)-(2,4-bichlorophenoxy)propionamido]-2',5'-dideoxy-5-ethyluridine,
5'-[2-(4-biphenylyl)acetamido]-2',5'-dideoxy-5-ethyluridine,
2',5'-dideoxy-5-ethyl-5'-[2(RS)-(2-phenylphenoxy)-propionamido]uridine,
1-[5-[2(RS)-(2,4-dichlorophenoxy)propionamido]-2,5-dideoxy-2-fluoro-β-D-arabinofuranosyl]-5-ethyluracil,
5'-[2(RS)-(2,4,5-trichlorophenoxy)propionamido]-2',5'-dideoxy-5-ethyluridine,
5'-[2(RS)-(4-chloro-2-nitrophenoxy)propionamido]-2',5'-dideoxy-5-ethyluridine,
5'-[2(RS)-(2,4-dichlorophenoxy)-2-phenylacetamido]-2',5'-deoxy-5-ethyluridine,
5'-[2(RS)-(2,4-dichloro-5-methoxyphenoxy)propionamido]-2',5'-dideoxy-5-ethyluridine and
5'-[2(RS)-(2,4-dichlorophenoxy)propionamido]-2',5'-dideoxy-5-propyluridine.

13. A compound according to claim 2, selected from the group consisting of
2',5'-Dideoxy-5-ethyl-5'-(2-phenylacetamido]uridine,
5'-(4-Bromobenzamido)-5'-deoxythymidine,
5'-deoxy-5'-(4-nitrobenzamido)thymidine, 5'-benzamido-5'-deoxythymidine,
5'-deoxy-5'-(2-fluorobenzamido)thymidine,
5'-deoxy-5'-(2-nitrobenzamido)thymidine,
5'-[2-(2-bromphenyl)acetamido]-5'-deoxythymidine,
5'-deoxy-5'-[2-(4-nitrophenyl)acetamido]thymidine,
5'-deoxy-5'-(2-phenylacetamido)thymidine,
5'-deoxy-5'-[2-(4-trifluoromethylphenyl)acetamido]thymidine,
5'-benzamido-2',5'-dideoxy-5-ethyluridine,
2',5'-dideoxy-5-ethyl-5'-(2-fluorobenzamido)uridine,
5'-(2-bromobenzamido)-2',5'-dideoxy-5-ethyluridine,
2',5'-dideoxy-5-ethyl-5'-(4-nitrobenzamido)uridine,
2',5'-dideoxy-5-ethyl-5'-(2-trifluoromethylbenzamido)uridine,
2',5'-dideoxy-5-ethyl-5'-[2-(2,6-dimethylphenyl)acetamido]uridine,
5'-[2(RS)-(2-bromophenyl)propionamido]-2',5'-dideoxy-5-ethyluridine,
5'-[2-(2-chloro-3-nitrophenyl)acetamido]-2',5'-dideoxy-5-ethyluridine,
5'-[2(RS)-(2,6-dichlorophenyl)propionamido]-2',5'-dideoxy-5-ethyluridine,
2',5'-dideoxy-5-ethyl-5'-[2-(3,5-dimethylphenyl)acetamido]uridine,
2',5'-dideoxy-5'-[2-(3,5-dimethoxyphenyl)acetamido]-5-ethyluridine,
2',5'-dideoxy-5-ethyl-5'-[2-(2,3,5,6-tetramethylphenyl)acetamido]uridine,
2',5'-dideoxy-5-ethyl-5'-[2-(2-methoxyphenyl)acetamido]uridine,
2',5'-dideoxy-5-ethyl-5'-[2-(2-nitrophenyl)acetamido]uridine,
5-bromo-5'-[2-(2-bromophenyl)acetamido]-2',5'-dideoxyuridine,
3'-O-butyryl-5'-[2-(2,6-dichlorophenyl)acetamido]-2',5'-dideoxy-5-ethyluridine,
2',5'-dideoxy-5'-[2-(2,6-dichlorophenyl)acetamido]-3'-O-(3,3-dimethylbutyryl)-5-ethyluridine,
5'-[2-(2,6-dichlorophenyl)acetamido]-2',5'-dideoxy-5-ethyl-3'-O-palmitoyluridine,
3'-O-acetyl-5'-[2-(2,6-dichlorophenyl)acetamido]-2',5'-dideoxy-5-ethyluridine,
3'-O-benzyl-5'-[2-(2,6-dichlorophenyl)acetamido]-2',5'-dideoxy-5-ethyluridine,
5'-[2-(2,6-dichlorophenyl)acetamido]-2',5'-dideoxy-3'-O-ethyl-5-ethyluridine,
2',3',5'-trideoxy-5'-[2-(2,6-dichlorophenyl)acetamido]-5-ethyluridine,
5'-[2-(2-aminophenyl)acetamido]-2',5'-dideoxy-5-ethyluridine,
5'-[2-(2-acetamidophenyl)acetamido]-3'-O-acetyl-2',5'-dideoxy-5-ethyluridine,
5'-[2-(2-acetamidophenyl)acetamido]-2',5'-dideoxy-5-ethyluridine,
2',5'-dideoxy-5-ethyl-5'-[2-(4-hydroxy-2,6-dimethylphenyl)acetamido]uridine,
5-(2-chloroethyl)-5'-[2-(2,6-dichlorophenyl)acetamido]-2',5'-dideoxyuridine,
5'-[2-(2-bromophenyl)-N-methylacetamido]-2',5'-dideoxy-5-ethyluridine,
5'-[2-(2,6-dichlorophenyl)-N-methylacetamido]-2',5'-dideoxy-5-ethyluridine,
5'-[2(RS)-(2-bromophenyl)-N-methylpropionamido]-2',5'-dideoxy-5-ethyluridine,
3'-O-acetyl-5'-[2-(2-bromophenyl)-N-methylacetamido]-2',5'-dideoxy-5-ethyluridine,
2',5'-dideoxy-5-ethyl-5'-(2-naphthalamido)uridine,
2',5'-dideoxy-5-ethyl-5'-(2-phenylbenzamido)uridine,
2',5'-dideoxy-5-ethyl-5'-(3-phenylpropionamido)uridine,
2',5'-dideoxy-5-ethyl-5'-(4-phenylbutyramido)uridine,
2',5'-dideoxy-5'-cinnamamido-5-ethyluridine,
2',5'-dideoxy-5-ethyl-5'-(3-phenyl-2-propynamido)uridine,
2',5'-dideoxy-5-ethyl-5'-[3-(phenylsulfonyl)propionamido]uridine,
5'-(2-bromocinnamamido)-2',5'-dideoxy-5-ethyluridine,
2',5'-dideoxy-5-ethyl-5'-[2-(2-thienyl)acetamido]uridine,
2',5'-dideoxy-5-ethyl-5'-[2-(3-thienyl)acetamido]uridine,
5'-(1-adamantylcarboxamido)-2',5'-dideoxy-5-ethyluridine,
2',5'-dideoxy-5-ethyl-5'-(2-pyridylcarboxamido)uridine,
2',5'-dideoxy-5-ethyl-5'-(3-pyridylcarboxamido)uridine,
2',5'-dideoxy-5-ethyl-5'-[2-(phenylsulfonyl)acetamido]uridine,
2',5'-dideoxy-5-ethyl-5'-(9-fluorenylcarboxamido)uridine,
3'-O-acetyl-2',5'-dideoxy-5-ethyl-5'-(9-fluorenylcarboxamido)uridine,
3'-O-butyryl-2',5'-dideoxy-5-ethyl-5'-(9-fluorenylcarboxamido)uridine,
2',5'-dideoxy-5-ethyl-3'-O-(3,3-dimethylbutyryl)-5'-(9-fluorenylcarboxamido)uridine,
2',5'-dideoxy-5-ethyl-5'-(9-fluorenylcarboxamido)-3'-O-(hexadecanoyl)uridine,
2',5'-dideoxy-5-ethyl-3'-O-(9-fluorenylcarbonyl)-5'-(9-fluorenylcarboxamido)uridine,
2',5'-dideoxy-5-ethyl-5'-(2-phenylbutyramido)uridine,
2',5'-dideoxy-5-ethyl-5'-(3-phenylbutyramido)uridine,
2',5'-dideoxy-5-ethyl-5'-(2,2-diphenylacetamido)uridine,
5'-(2-cyclohexyl-2-phenylacetamido)-2',5'-dideoxy-5-ethyluridine,
2',5'-dideoxy-5-ethyl-5'-(triphenylacetamido)uridine,
2',5'-dideoxy-5-ethyl-5'-(2-methyl-2-phenylpropionamido)uridine,
2',5'-dideoxy-5-ethyl-5'-[2(RS)-phenylpropionamido]uridine,
5'-[2(RS)-(2,4-dichlorophenoxy)propionamido]-2',5'-dideoxy-5-ethyluridine, 5'-[2(RS)-(2,6-dichlorophenoxy)propionamido]-2',5'-dideoxy-5-ethyluridine,
5'-[2(RS)-(3,5-dichlorophenoxy)propionamido]-2',5'-dideoxy-5-ethyluridine,
5'-[2(RS)-(2-chlorophenoxy)propionamido]-2',5'-dideoxy-5-ethyluridine,
5'-[2-(2,6-dichlorophenoxy)acetamido]-2',5'-dideoxy-5-ethyluridine,
5'-[2-(2,4-dichlorophenoxy)acetamido]-2',5'-dideoxy-5-ethyluridine,
5'-[4-(2,6-dichlorophenoxy)butyramido]-2',5'-dideoxy-5-ethyluridine,
5'-[6-(2,6-dichlorophenoxy)hexanamido]-2',5'-dideoxy-5-ethyluridine,
5'-[5-(2,6-dichlorophenoxy)valeramido]-2',5'-dideoxy-5-ethyluridine,
5'-[2(RS)-(2-chloro-4-nitrophenoxy)propionamido]-2',5'-dideoxy-5-ethyluridine, 5'-[2(RS)-(2-chloro-4-phenylphenoxy)pro-
    pionamido]-2',5'-dideoxy-5-ethyluridine,
5-bromo-5'-[2-(2-bromophenyl)acetamido]-2',5'-
    dideoxycytidine and
5'-[2-(2-bromophenyl)acetamido]-2',5'-dideoxy-5-
    ethylcytidine.

14. A compound according to claim 1, selected from the group consisting of
5'-[2-(2,6-Dichlorophenyl)acetamido]-5'-deoxy-
    thymidine,
5-bromo-5'-[2(RS)-(2,4-dichlorophenoxy)pro-
    pionamido]-2',5'-dideoxyuridine,
5-bromo-5'-[2-(2,6-dichlorophenyl)acetamido]-2',5'-
    dideoxyuridine,
5'-benzamido-5-bromo-2',5'-dideoxyuridine,
5'-[2(RS)-(2,4-dichlorophenoxy)propionamido]-2',5'-
    dideoxy-5-iodouridine,
5'-[2(RS)-(2,4,5-trichlorophenoxy)propionamido]-
    2',5'-dideoxy-5-iodouridine,
5'-[2-(2,6-dichlorophenyl)acetamido]-2',5'-dideoxy-5-
    iodouridine,
3'-O-benzyl-5'-[2(RS)-(2,4-dichlorophenoxy)pro-
    pionamido]-2',5'-dideoxy-5-ethyluridine,
5'-[2(RS)-(2,4-dichlorophenoxy)propionamido]-2',5'-
    dideoxy-3'-O-ethyl-5-ethyluridine,
5'-[2(RS)-(2,4-dichlorophenoxy)-N-methylpro-
    pionamido]-2',5'-dideoxy-5-ethyluridine,
5'-[2(R)-(2,4-dichlorophenoxy)propionamido]-2',5'-
    dideoxy-5-ethyluridine,
5'-[2(S)-(2,4-dichlorophenoxy)propionamido]-2',5'-
    dideoxy-5-ethyluridine,
5'-[2(RS)-(2,4-dichlorophenoxy)butyramido]-2',5'-
    dideoxy-5-ethyluridine,
5'-[2(RS)-(4-acetamido-2-chlorophenoxy)pro-
    pionamido]-2',5'-dideoxy-5-ethyluridine,
5'-[2(RS)-(2-chloro-4-methoxyphenoxy)pro-
    pionamido]-2',5'-dideoxy-5-ethyluridine,
2',5'-dideoxy-5-ethyl-5'-[2(RS)-(2-methylbi-
    phenylyloxy)propionamido]uridine,
5'-[2(RS)-(2,4-dichlorophenoxy)propionamido]-5'-
    deoxythymidine,
5'-[2-(2,4-dichlorophenoxy)-2-methylpropionamido]-
    2',5'-dideoxy-5-ethyluridine,
2',5'-dideoxy-5-ethyl-5'-[2(RS)-phenoxypro-
    pionamido]uridine,
2',5'-dideoxy-5-ethyl-5'-[2(RS)-(2-fluorophenoxy)-
    propionamido]uridine,
2',5'-dideoxy-5-ethyl-5'-[2(RS)-(2-trifluoromethyl-
    phenoxy)propionamido]uridine,
1-[5-[2(RS)-(2,4-dichlorophenoxy)propionamido]-
    2,5-dideoxy-2-fluoro-β-D-arabinofuranosyl]thy-
    mine,
5'-[2(RS)-(2,4-dichlorophenylsulfinyl)pro-
    pionamido]-2',5'-dideoxy-5-ethyluridine,
5'-[2(RS)-(2,4-dichlorophenylsulfonyl)pro-
    pionamido]-2',5'-dideoxy-5-ethyluridine,
5'-[2-(2,6-dichlorophenylacetamido)ethyl]-2',5'-
    dideoxy-5-ethyluridine,
5'-[2-[2(RS)-(2,4,5-trichlorophenoxy)pro-
    pionamido]ethyl]-2',5'-dideoxy-5-ethyluridine,
5'-[2-[2(RS)-(2,4-dichlorophenoxy)propionamido]e-
    thyl]-2',5'-dideoxy-5-ethyluridine,
5'-[2(RS)-(2,6-dichlorobenzyl)propionamido]-2',5'-
    dideoxy-5-ethyluridine,
5'-[2(RS)-(2,4-dichlorobenzyl)propionamido]-2',5'-
    dideoxy-5-ethyluridine,
5'-[5-chloro-2,3-dihydro-2(RS)-benzofuranylcarbox-
    amido]-2',5'-dideoxy-5-ethyluridine,
5-(6-chloro-2H-1-benzopyran-2-ylcarboxamido)-
    2',5'-dideoxy-5-ethyluridine,
5'-[2-(4-benzyloxy-2,6-dimethylphenyl)acetamido]-
    2',5'-dideoxy-5-ethyluridine,
3'-O-acetyl-5'-[2-(4-benzyloxy-2,6-dimethylphenyl-
    )acetamido]-2',5'-dideoxy-5-ethyluridine,
3'-O-acetyl-2',5'-dideoxy-5-ethyl-5'-[2-(4-hydroxy-
    2,6-dimethylphenyl)acetamido]uridine,
2',5'-dideoxy-5-ethyl-5'-[2-(2,6-dimethyl-4-phos-
    phatophenyl)acetamido]uridine,
5-(2-chloroethyl)-2',5'-dideoxy-5'-[2-(2,4-dichloro-
    phenoxy)propionamido]uridine,
5'-benzamido-5-(2-chloroethyl)-2',5'-dideoxyuridine,
5-(2-chloroethyl)-5'-[2-(2,4,5-trichlorophenoxy)pro-
    pionamido]-2',5'-dideoxyuridine,
5'-[2-(2,6-dichlorophenyl)acetamido]-2',5'-dideoxy-5-
    propyluridine,
5'-[2(RS)-(2,4-dichlorophenoxy)propionamido]-2',5'-
    dideoxy-5-propyluridine, and
5-acetyl-5'-[2-(2,6-dichlorophenyl)acetamido]-2',5'-
    dideoxyuridine.

15. A pharmaceutical composition comprising an effective amount of a compound of formula

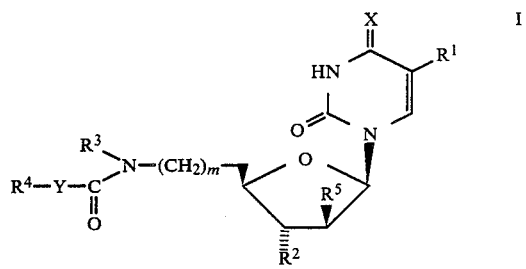

wherein
R¹ is halogen, $C_{1-4}$-alkyl, halo-($C_{1-4}$-alkyl) or $C_{2-4}$-alkanoyl,
R² is hydrogen, hydroxy, $C_{1-4}$-alkoxy-$C_{1-4}$-alkylthio, phenyl-($C_{1-4}$-alkoxy) or $C_{2-4}$-alkanoyloxy,
R³ is hydrogen or $C_{1-4}$-alkyl,
R⁴ is a carbocyclic group selected from the group consisting of 2-biphenylyl, 4-biphenylyl, 3-chloro-4-biphenylyl, 1-naphthyl, 2-naphthyl, cyclopentyl, cyclohexyl, adamantyl, indanyl, fluorenyl and phenyl which may be substituted by one or more substituents selected from the group consisting of halogen, hydroxy, $C_{1-4}$-alkyl, $C_{1-4}$-alkoxy, trifluoromethyl, phenyl, $C_{1-4}$-alkylphenyl, halophenyl, nitro, amino, $C_{2-4}$-alkanoylamino, benzyloxy and O-phosphate, or is a heterocyclic group selected from the group consisting of 2-furyl, 2-thienyl, 3-thienyl, 2-pyridyl, 3-pyridyl, 2-benzofuranyl, 2,3-dihydro-2-benzofuranyl, 2-benzothienyl, 2-quinolyl and 2-benzopyranyl
R⁵ is hydrogen or fluorine,
m stands for zero, 1 or 2,
X is O and Y is a direct bond, —CH=CH—, —C≡C— or a group of the formula of $$—(Z)_n—A—$$  (a)

in which A is a $C_{1-8}$-alkylene group which may be substituted by one or two phenyl groups,
Z is O, S, SO or SO₂ and n stands for zero or 1, with the proviso that R¹ is different from iodine, when R² is hydroxy or benzyloxy, R³ is hydrogen, R⁴ is unsubstituted phenyl, $R^5$ is hydrogen, m is zero, X is O, and Y is a direct bond, or a tautomer thereof, and an inert carrier.

16. A pharmaceutical composition according to claim 15, $R^1$ is fluorine, chlorine, bromine, $C_{1-4}$-alkyl or halo-($C_{1-4}$-alkyl), $R^4$ is a carbocyclic group as defined in claim 1, $R^5$ is hydrogen and m is zero.

17. A pharmaceutical composition according to claim 16, wherein $R^1$ is $C_{1-4}$-alkyl.

18. A pharmaceutical according to claim 17, wherein $R^2$ is hydroxy.

19. A pharmaceutical composition according to claim 18, wherein $R^3$ is hydrogen.

20. A pharmaceutical composition according to claim 19, wherein $R^4$ is phenyl which may be substituted by one or more substituents selected from the group consisting of halogen, $C_{1-4}$-alkyl, $C_{1-4}$-alkoxy, trifluoromethyl, phenyl and nitro.

21. A pharmaceutical composition according to claim 20, wherein m is zero.

22. A pharmaceutical composition according to claim 21, wherein X is O.

23. A pharmaceutical composition according to claim 22, wherein Y is a group of formula (a) as defined in claim 1.

24. A pharmaceutical composition according to claim 21, wherein $R^1$ is ethyl, $R^2$ is hydroxy, $R^3$ is hydrogen, $R^4$ is 2-bromophenyl, 2,6-dichlorophenyl or 4-biphenylyl, m is zero, X is O and Y is a group of formula (a) as defined in claim 1 in which A is —$CH_2$ or —CH($CH_3$)— and n is zero.

25. A pharmaceutical composition according to claim 21, wherein $R^1$ is ethyl or propyl, $R^2$ is hydroxy, $R^3$ is hydrogen, $R^4$ is 2-biphenylyl, 2,4-dichlorophenyl, 2,4,5-trichlorophenyl, 4-chloro-2-nitrophenyl or 2,4-dichloro-5-methoxyphenyl, m stands for zero, X is O and Y is a group of formula (a) in which A is —CH($CH_3$)— or —CH(phenyl)—, Z is O and n is 1.

* * * * *